US012584139B2

(12) United States Patent
Kawata et al.

(10) Patent No.: US 12,584,139 B2
(45) Date of Patent: Mar. 24, 2026

(54) NUCLEIC ACID CONSTRUCT SET, KIT, DETECTION METHOD AND METHOD FOR PREDICTING DRUG EFFECT

(71) Applicant: KABUSHIKI KAISHA TOSHIBA, Tokyo (JP)

(72) Inventors: Shigehisa Kawata, Niiza (JP); Mitsuko Ishihara, Setagaya (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 768 days.

(21) Appl. No.: 17/930,890

(22) Filed: Sep. 9, 2022

(65) Prior Publication Data

US 2023/0092732 A1 Mar. 23, 2023

Related U.S. Application Data

(63) Continuation of application No. PCT/JP2021/044292, filed on Dec. 2, 2021.

(30) Foreign Application Priority Data

Dec. 4, 2020 (JP) ................................ 2020-201985

(51) Int. Cl.

| | |
|---|---|
| ***C12N 15/63*** | (2006.01) |
| ***C12Q 1/6883*** | (2018.01) |
| ***C12Q 1/6897*** | (2018.01) |
| ***G01N 33/50*** | (2006.01) |
| *G01N 21/75* | (2006.01) |

(52) U.S. Cl.

CPC ........... *C12N 15/63* (2013.01); *C12Q 1/6883* (2013.01); *C12Q 1/6897* (2013.01); *G01N 33/5044* (2013.01); *G01N 21/75* (2013.01); *G01N 2800/52* (2013.01)

(58) Field of Classification Search

None

See application file for complete search history.

(56) References Cited

U.S. PATENT DOCUMENTS

| | | | | |
|---|---|---|---|---|
| 6,284,541 | B1 | 9/2001 | Auer et al. | |
| 10,945,956 | B2 * | 3/2021 | Ishihara | C12N 15/00 |
| 11,548,857 | B2 * | 1/2023 | Ishihara | C07D 251/04 |
| 2011/0236976 | A1 | 9/2011 | Steigerwald | |
| 2015/0037892 | A1 | 2/2015 | Wiessenhaan et al. | |
| 2017/0283879 | A1 | 10/2017 | Abkevich et al. | |
| 2020/0000723 | A1 * | 1/2020 | Ishihara | A61K 47/16 |
| 2021/0102159 | A1 | 4/2021 | Saruwatari et al. | |
| 2021/0404021 | A1 | 12/2021 | Kawata et al. | |

FOREIGN PATENT DOCUMENTS

| | | | | |
|---|---|---|---|---|
| JP | 2001-523442 | A | 11/2001 | |
| JP | 2006-141329 | A | 6/2006 | |
| JP | 2012-509073 | A | 4/2012 | |
| JP | 2016-523511 | A | 8/2016 | |
| JP | 2017-533693 | A | 11/2017 | |
| WO | WO 2010/057650 | A1 | 5/2010 | |
| WO | WO 2014/165785 | A2 | 10/2014 | |
| WO | WO-2016196887 | A1 * | 12/2016 | A01K 67/0275 |
| WO | WO 2019/131961 | A1 | 7/2019 | |
| WO | WO 2021/079522 | A1 | 4/2021 | |

OTHER PUBLICATIONS

Rajaee et al. Plant Biotechnol J. Nov. 2017;15(11):1420-1428. Epub Apr. 20, 2017 (Year: 2017).*

Kawano et al. Engineered pairs of distinct photoswitches for optogenetic control of cellular proteins. Nat Commun 6, 6256 (2015) (Year: 2015).*

Wang et al. Cell culture and cell based sensor on CMOS, 2014 IEEE Biomedical Circuits and Systems Conference (BioCAS) Proceedings, Lausanne, Switzerland, 2014, pp. 468-471) (Year: 2014).*

Yoshimi et al. Photoactivatable Cre knock-in mice for spatiotemporal control of genetic engineering in vivo. Lab Invest 101, 125-135 (Sep. 2020) (Year: 2020).*

Morikawa et al. Photoactivatable Cre recombinase 3.0 for in vivo mouse applications. Nat Commun 11, 2141 (May 1, 2020) (Year: 2020).*

Written Opinion issued Feb. 24, 2022 in PCT/JP2021/044292 filed on Dec. 2, 2021, 6 pages.

Ransburgh et al., "Identification of Breast Tumor Mutations in BRCA1 That Abolish Its Function in Homologous DNA Recombination", Cancer Research, vol. 70, No. 3, 2010, pp. 988-995, DOI: 10.1158/0008-5472.CAN-09-2850.

Telli et al., "Homologous Recombination Deficiency (HRD) Score Predicts Response to Platinum-Containing Neoadjuvant Chemotherapy in Patients with Triple-Negative Breast Cancers" (Author Manuscript), Clinical Cancer Research, vol. 22, No. 15, 2016, 21 pages, DOI: 10.1158/1078-0432.CCR-15-2477.

Yoshino et al., "Evaluation of site-specific homologous recombination activity of BRCA1 by direct quantitation of gene editing efficiency", Scientific Reports, vol. 9, No. 1, 2019, 12 pages, DOI: 10.1038/s41598-018-38311-x.

Yoshimi, Kazuto et al., "Photoactivatable Cre knock-in mice for spatiotemporal control of genetic engineering in vivo", Laboratory Investigation, vol. 101, 2021, pp. 125-135.

Japanese Decision to Grant a Patent issued Oct. 8, 2024 in Japanese Patent Application No. 2020-201985 (with unedited computer-generated English translation), 46 pages.

* cited by examiner

*Primary Examiner* — Christopher M Babic

(74) *Attorney, Agent, or Firm* — Oblon, McClelland, Maier & Neustadt, L.L.P.

(57) ABSTRACT

According to one embodiment, a set of nucleic acid constructs which detects a DNA homologous recombination deficiency includes a first nucleic acid construct and a second nucleic acid construct. The first nucleic acid construct includes a first promoter sequence and a cleaved Cre gene ligated to downstream of the first promoter sequence. The second nucleic acid construct includes a second promoter sequence, a first loxP sequence ligated to downstream of the second promoter sequence, a reporter gene ligated to downstream of the first loxP sequence, and a second loxP sequence ligated to downstream of the reporter gene.

18 Claims, 6 Drawing Sheets

Specification includes a Sequence Listing.

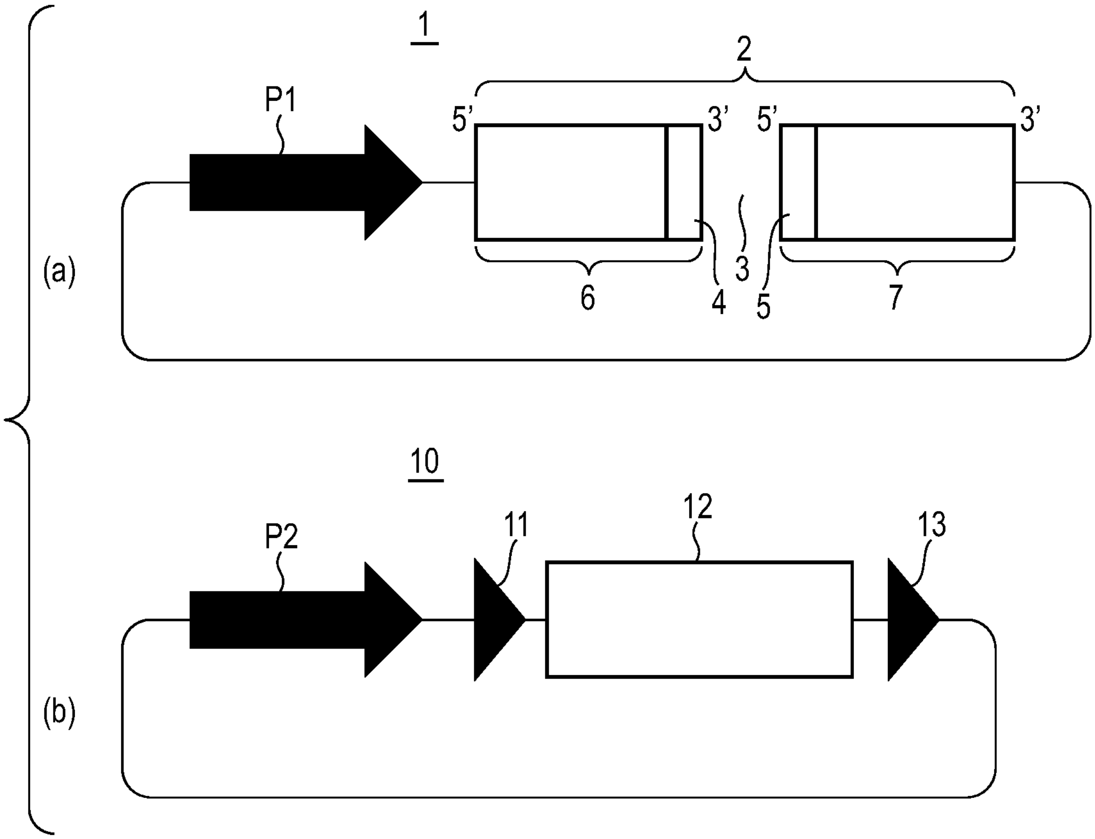
F I G. 1
| | |
|---|---|
| S1 | Transfection step of transfecing first nucleic acid construct and second nucleic acid construct into test cells |
| S2 | Culture step of culturing test cells |
| S3 | Detection step of detecting activity of reporter protein expressed from reporter gene |
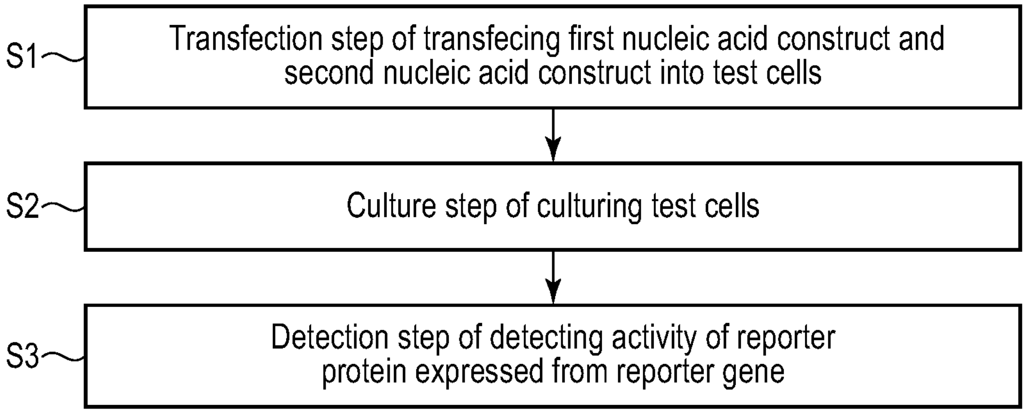
F I G. 2

In test cells having DNA homologous recombination function
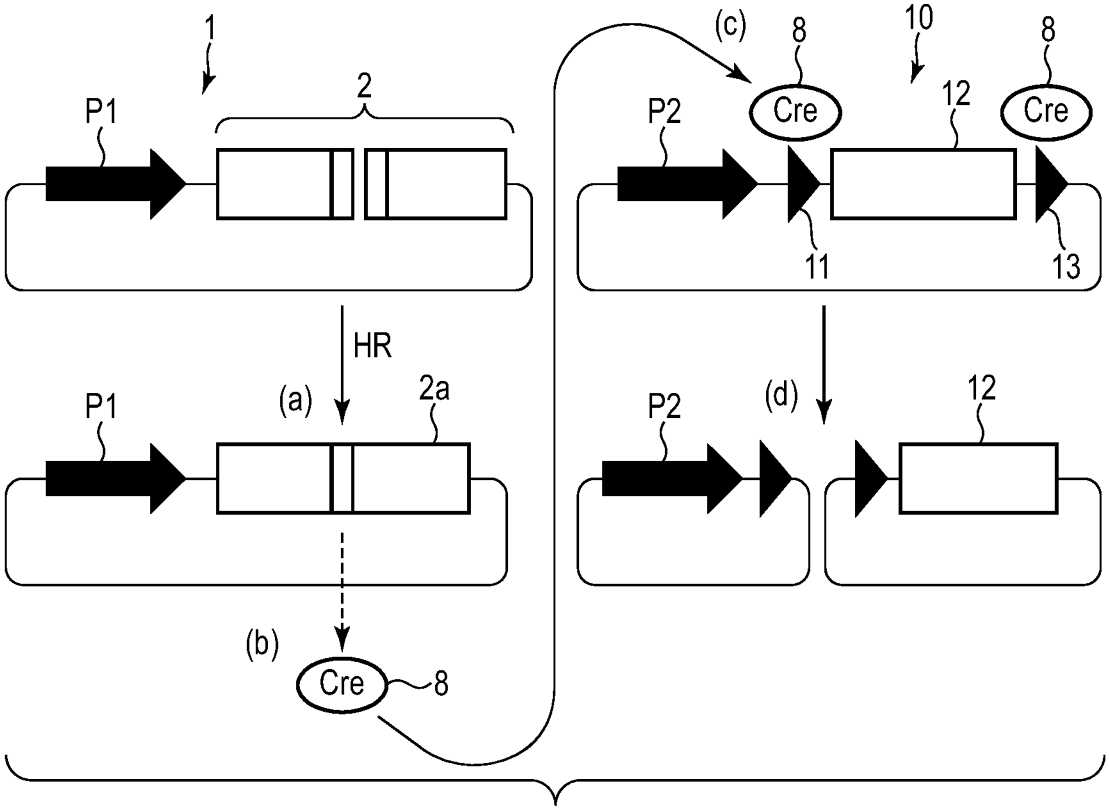
F I G. 3
In test cells having DNA homologous recombination deficiency
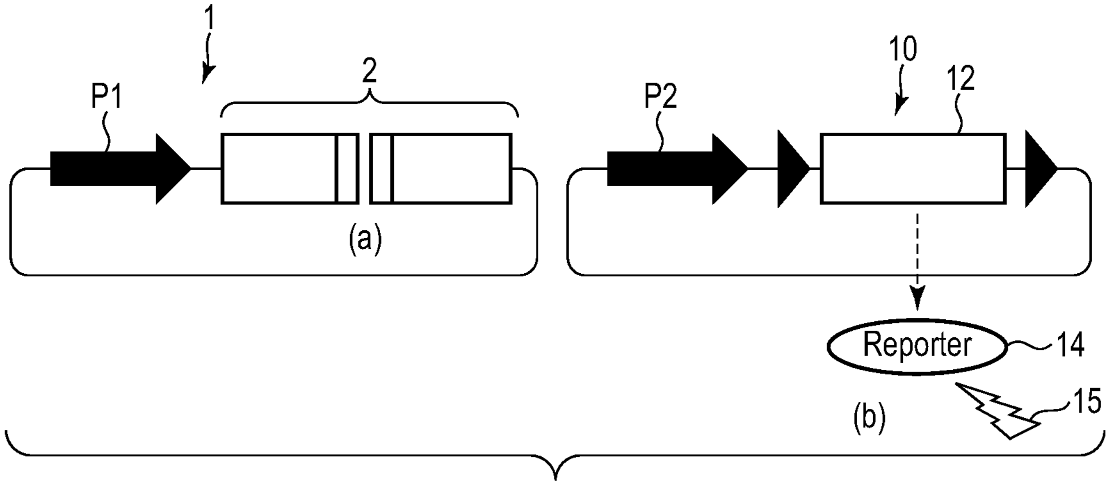
F I G. 4

| S11 | Transfection step |
| S12 | Culture step |
| S13 | Detection step |
| S14 | Calculation step of calculating positive rate of cells having DNA homologous recombination deficiency included in test cells based on detection result |
| S15 | Prediction step of predicting effect of DNA-damaging anticancer agent on cancer in subject based on the positive rate |
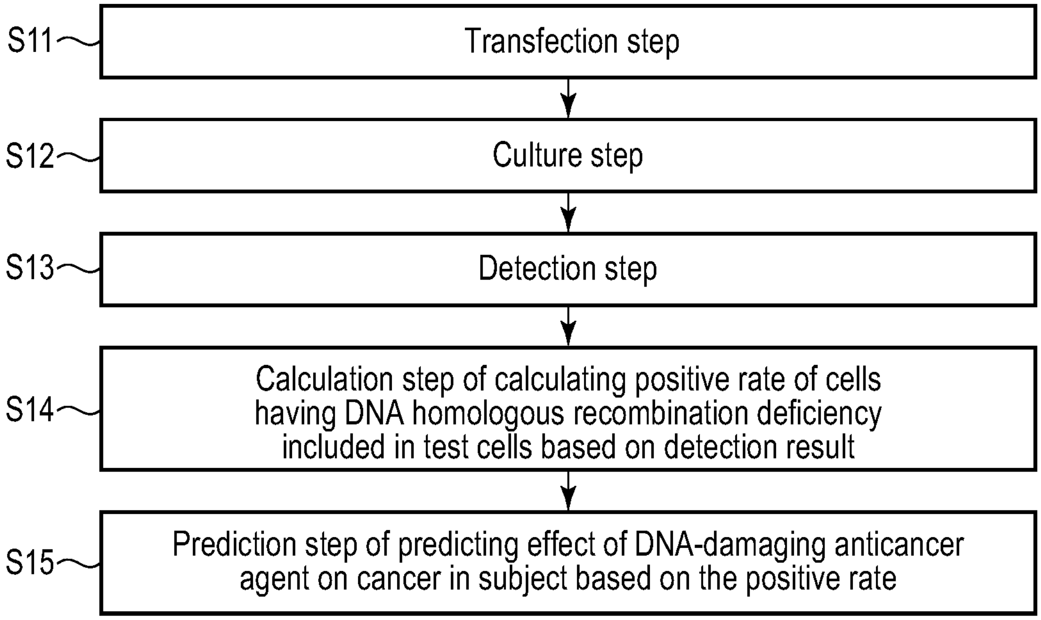
F I G. 6
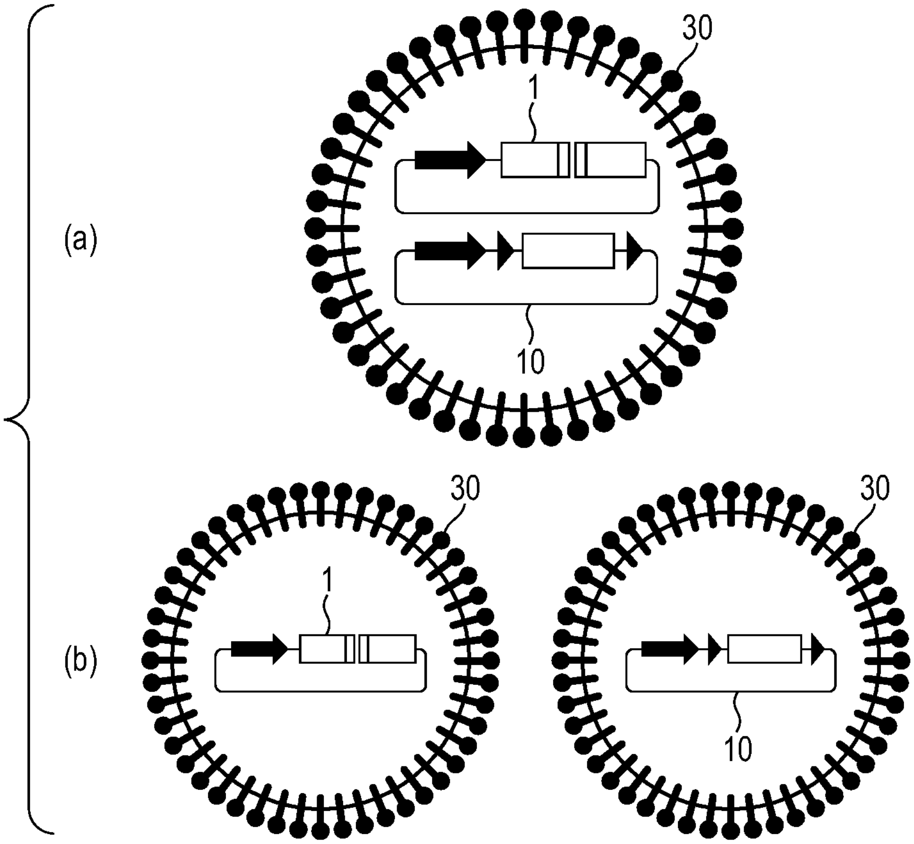
F I G. 7

SEQUENCE LISTING

```
Sequence total quantity: 15
SEQ ID NO: 1            moltype = DNA  length = 1032
FEATURE                 Location/Qualifiers
source                  1..1032
                        mol_type = other DNA
                        note = Bacteriophage
                        organism = unidentified
SEQUENCE: 1
atgtccaatt tactgaccgt acaccaaaat ttgcctgcat taccggtcga tgcaacgagt  60
gatgaggttc gcaagaacct gatggacatg ttcagggatc gccaggcgtt ttctgagcat  120
acctggaaaa tgcttctgtc cgtttgccgg tcgtgggcgg catggtgcaa gttgaataac  180
cggaaatggt ttcccgcaga acctgaagat gttcgcgatt atcttctata tcttcaggcg  240
cgcggtctgg cagtaaaaac tatccagcaa catttgggcc agctaaacat gcttcatcgt  300
cggtccgggc tgccacgacc aagtgacagc aatgctgttt cactggttat gcggcggatc  360
cgaaaagaaa acgttgatgc cggtgaacgt gcaaaacagg ctctagcgtt cgaacgcact  420
gatttcgacc aggttcgttc actcatggaa aatagcgatc gctgccagga tatacgtaat  480
ctggcatttc tggggattgc ttataacacc ctgttacgta tagccgaaat tgccaggatc  540
agggttaaag atatctcacg tactgacggt gggagaatgt taatccatat tggcagaacg  600
aaaacgctgg ttagcaccgc aggtgtagag aaggcactta gcctgggggt aactaaactg  660
gtcgagcgat ggatttccgt ctctggtgta gctgatgatc cgaataacta cctgttttgc  720
cgggtcagaa aaaatggtgt tgccgcgcca tctgccacca gccagctatc aactcgcgcc  780
ctggaaggga tttttgaagc aactcatcga ttgatttacg gcgctaagga tgactctggt  840
cagagatacc tggcctggtc tggacacagt gcccgtgtcg gagccgcgcg agatatggcc  900
cgcgctggag tttcaatacc ggagatcatg caagctggtg gctggaccaa tgtaaatatt  960
gtcatgaact atatccgtac cctggatagt gaaacagggg caatggtgcg cctgctggaa  1020
gatggcgatt ag                                                      1032

SEQ ID NO: 2            moltype = DNA  length = 10
FEATURE                 Location/Qualifiers
source                  1..10
                        mol_type = other DNA
                        note = Bacteriophage
                        organism = unidentified
SEQUENCE: 2
ttatgcggcg                                                         10

SEQ ID NO: 3            moltype = DNA  length = 356
FEATURE                 Location/Qualifiers
misc_feature            1..356
                        note = 5' -side fragment
source                  1..356
                        mol_type = other DNA
                        organism = synthetic construct
SEQUENCE: 3
atgtccaatt tactgaccgt acaccaaaat ttgcctgcat taccggtcga tgcaacgagt  60
gatgaggttc gcaagaacct gatggacatg ttcagggatc gccaggcgtt ttctgagcat  120
acctggaaaa tgcttctgtc cgtttgccgg tcgtgggcgg catggtgcaa gttgaataac  180
cggaaatggt ttcccgcaga acctgaagat gttcgcgatt atcttctata tcttcaggcg  240
cgcggtctgg cagtaaaaac tatccagcaa catttgggcc agctaaacat gcttcatcgt  300
cggtccgggc tgccacgacc aagtgacagc aatgctgttt cactggttat gcggcg      356

SEQ ID NO: 4            moltype = DNA  length = 686
FEATURE                 Location/Qualifiers
misc_feature            1..686
                        note = 3'-side fragment
source                  1..686
                        mol_type = other DNA
                        organism = synthetic construct
SEQUENCE: 4
ttatgcggcg gatccgaaaa gaaaacgttg atgccggtga acgtgcaaaa caggctctag  60
cgttcgaacg cactgatttc gaccaggttc gttcactcat ggaaaatagc gatcgctgcc  120
aggatatacg taatctggca tttctgggga ttgcttataa caccctgtta cgtatagccg  180
aaattgccag gatcagggtt aaagatatct cacgtactga cggtgggaga atgttaatcc  240
atattggcag aacgaaaacg ctggttagca ccgcaggtgt agagaaggca cttagcctgg  300
gggtaactaa actggtcgag cgatggattt ccgtctctgg tgtagctgat gatccgaata  360
actacctgtt ttgccgggtc agaaaaaatg gtgttgccgc gccatctgcc accagccagc  420
tatcaactcg cgccctggaa gggatttttg aagcaactca tcgattgatt tacggcgcta  480
aggatgactc tggtcagaga tacctggcct ggtctggaca cagtgcccgt gtcggagccg  540
cgcgagatat ggcccgcgct ggagtttcaa taccggagat catgcaagct ggtggctgga  600
ccaatgtaaa tattgtcatg aactatatcc gtaacctgga tagtgaaaca ggggcaatgg  660
tgcgcctgct ggaagatggc gattag                                       686
```

-continued

```
SEQ ID NO: 5            moltype = DNA  length = 20
FEATURE                 Location/Qualifiers
source                  1..20
                        mol_type = other DNA
                        note = Bacteriophage
                        organism = unidentified
SEQUENCE: 5
ttatgcggcg gatccgaaaa                                             20

SEQ ID NO: 6            moltype = DNA  length = 30
FEATURE                 Location/Qualifiers
source                  1..30
                        mol_type = other DNA
                        note = Bacteriophage
                        organism = unidentified
SEQUENCE: 6
ttatgcggcg gatccgaaaa gaaaacgttg                                  30

SEQ ID NO: 7            moltype = DNA  length = 34
FEATURE                 Location/Qualifiers
source                  1..34
                        mol_type = other DNA
                        note = Bacteriophage
                        organism = unidentified
SEQUENCE: 7
ataacttcgt atagcataca ttatacgaag ttat                             34

SEQ ID NO: 8            moltype = DNA  length = 550
FEATURE                 Location/Qualifiers
source                  1..550
                        mol_type = other DNA
                        organism = Oplophorus gracilirostris
SEQUENCE: 8
agcttggcaa tccggtactg ttggtaaagc caccatggtc ttcacactcg aagatttcgt  60
tggggactgg cgacagacag ccggctacaa cctggaccaa gtccttgaac agggaggtgt  120
gtccagtttg tttcagaatc tcggggtgtc cgtaactccg atccaaagga ttgtcctgag  180
cggtgaaaat gggctgaaga tcgacatcca tgtcatcatc ccgtatgaag gtctgagcgg  240
cgaccaaatg ggccagatcg aaaaaatttt taaggtggtg taccctgtgg atgatcatca  300
ctttaaggtg atcctgcact atggcacact ggtaatcgac ggggttacgc cgaacatgat  360
cgactatttc ggacggccgt atgaaggcat cgccgtgttc gacggcaaaa agatcactgt  420
aacagggacc ctgtggaacg gcaacaaaat tatcgacgag cgcctgatca accccgacgg  480
ctccctgctg ttccgagtaa ccatcaacgg agtgaccggc tggcggctgt gcgaacgcat  540
tctggcgtaa                                                        550

SEQ ID NO: 9            moltype = DNA  length = 1128
FEATURE                 Location/Qualifiers
misc_feature            1..1128
                        note = vector 1-10
source                  1..1128
                        mol_type = other DNA
                        organism = synthetic construct
SEQUENCE: 9
agtgaaccgt cagatcctcg agatctgcga tctaagtaat gtccaattta ctgaccgtac  60
accaaaattt gcctgcatta ccggtcgatg caacgagtga tgaggttcgc aagaacctga  120
tggacatgtt cagggatcgc caggcgtttt ctgagcatac ctggaaaatg cttctgtccg  180
tttgccggtc gtgggcggca tggtgcaagt tgaataaccg gaaatggttt cccgcagaac  240
ctgaagatgt tcgcgattat cttctatatc ttcaggcgcg cggtctggca gtaaaaacta  300
tccagcaaca tttgggccag ctaaacatgc ttcatcgtcg gtccgggctg ccacgaccaa  360
gtgacagcaa tgctgtttca ctggttatgc ggcggggccc gttaacgcta gcttatgcgg  420
cggatccgaa aagaaaacgt tgatgccggt gaacgtgcaa aacaggctct agcgttcgaa  480
cgcactgatt tcgaccaggt tcgttcactc atggaaaata gcgatcgctg ccaggatata  540
cgtaatctgg catttctggg gattgcttat aacaccctgt tacgtatagc cgaaattgcc  600
aggatcaggg ttaaagatat ctcacgtact gacggtggga gaatgttaat ccatattggc  660
agaacgaaaa cgctggttag caccgcaggt gtagagaagg cacttagcct gggggtaact  720
aaactggtcg agcgatggat ttccgtctct ggtgtagctg atgatccgaa taactacctg  780
ttttgccggg tcagaaaaaa tggtgttgcc gcgccatctg ccaccagcca gctatcaact  840
cgcgccctgg aagggatttt tgaagcaact catcgattga tttacggcgc taaggatgac  900
tctggtcaga gatacctggc ctggtctgga cacagtgccc gtgtcggagc cgcgcgagat  960
atggcccgcg ctggagtttc aataccggag atcatgcaag ctggtggctg gaccaatgta  1020
aatattgtca tgaactatat ccgtaacctg gatagtgaaa caggggcaat ggtgcgcctg  1080
ctggaagatg gcgattaggg ccgcgactct agaactagtg gatccccc               1128

SEQ ID NO: 10           moltype = DNA  length = 1138
FEATURE                 Location/Qualifiers
misc_feature            1..1138
                        note = vector 1-20
source                  1..1138
                        mol_type = other DNA
                        organism = synthetic construct
```

-continued

```
SEQUENCE: 10
agtgaaccgt cagatcctcg agatctgcga tctaagtaat gtccaattta ctgaccgtac  60
accaaaattt gcctgcatta ccggtcgatg caacgagtga tgaggttcgc aagaacctga  120
tggacatgtt cagggatcgc caggcgtttt ctgagcatac ctggaaaatg cttctgtccg  180
tttgccggtc gtgggcggca tggtgcaagt tgaataaccg gaaatggttt cccgcagaac  240
ctgaagatgt tcgcgattat cttctatatc ttcaggcgcg cggtctggca gtaaaaacta  300
tccagcaaca tttgggccag ctaaacatgc ttcatcgtcg gtccgggctg ccacgaccaa  360
gtgacagcaa tgctgtttca ctggttatgc ggcggatccg aaaagggccc gttaacgcta  420
gcttatgcgg cggatccgaa aagaaaacgt tgatgccggt gaacgtgcaa aacaggctct  480
agcgttcgaa cgcactgatt tcgaccaggt tcgttcactc atggaaaata gcgatcgctg  540
ccaggatata cgtaatctgg catttctggg gattgcttat aacaccctgt tacgtatagc  600
cgaaattgcc aggatcaggg ttaaagatat ctcacgtact gacggtggga gaatgttaat  660
ccatattggc agaacgaaaa cgctggttag caccgcaggt gtagagaagg cacttagcct  720
gggggtaact aaactggtcg agcgatggat ttccgtctct ggtgtagctg atgatccgaa  780
taactacctg ttttgccggg tcagaaaaaa tggtgttgcc gcgccatctg ccaccagcca  840
gctatcaact cgcgccctgg aagggatttt tgaagcaact catcgattga tttacggcgc  900
taaggatgac tctggtcaga gatacctggc ctggtctgga cacagtgccc gtgtcggagc  960
cgcgcgagat atggcccgcg ctggagtttc aataccggag atcatgcaag ctggtggctg  1020
gaccaatgta aatattgtca tgaactatat ccgtaacctg gatagtgaaa caggggcaat  1080
ggtgcgcctg ctggaagatg gcgattaggg ccgcgactct agaactagtg gatccccc    1138

SEQ ID NO: 11          moltype = DNA  length = 1148
FEATURE                Location/Qualifiers
misc_feature           1..1148
                       note = vector 1-30
source                 1..1148
                       mol_type = other DNA
                       organism = synthetic construct
SEQUENCE: 11
agtgaaccgt cagatcctcg agatctgcga tctaagtaat gtccaattta ctgaccgtac  60
accaaaattt gcctgcatta ccggtcgatg caacgagtga tgaggttcgc aagaacctga  120
tggacatgtt cagggatcgc caggcgtttt ctgagcatac ctggaaaatg cttctgtccg  180
tttgccggtc gtgggcggca tggtgcaagt tgaataaccg gaaatggttt cccgcagaac  240
ctgaagatgt tcgcgattat cttctatatc ttcaggcgcg cggtctggca gtaaaaacta  300
tccagcaaca tttgggccag ctaaacatgc ttcatcgtcg gtccgggctg ccacgaccaa  360
gtgacagcaa tgctgtttca ctggttatgc ggcggatccg aaaagaaaac gttggggccc  420
gttaacgcta gcttatgcgg cggatccgaa aagaaaacgt tgatgccggt gaacgtgcaa  480
aacaggctct agcgttcgaa cgcactgatt tcgaccaggt tcgttcactc atggaaaata  540
gcgatcgctg ccaggatata cgtaatctgg catttctggg gattgcttat aacaccctgt  600
tacgtatagc cgaaattgcc aggatcaggg ttaaagatat ctcacgtact gacggtggga  660
gaatgttaat ccatattggc agaacgaaaa cgctggttag caccgcaggt gtagagaagg  720
cacttagcct gggggtaact aaactggtcg agcgatggat ttccgtctct ggtgtagctg  780
atgatccgaa taactacctg ttttgccggg tcagaaaaaa tggtgttgcc gcgccatctg  840
ccaccagcca gctatcaact cgcgccctgg aagggatttt tgaagcaact catcgattga  900
tttacggcgc taaggatgac tctggtcaga gatacctggc ctggtctgga cacagtgccc  960
gtgtcggagc cgcgcgagat atggcccgcg ctggagtttc aataccggag atcatgcaag  1020
ctggtggctg gaccaatgta aatattgtca tgaactatat ccgtaacctg gatagtgaaa  1080
caggggcaat ggtgcgcctg ctggaagatg gcgattaggg ccgcgactct agaactagtg  1140
gatccccc                                                          1148

SEQ ID NO: 12          moltype = DNA  length = 56
FEATURE                Location/Qualifiers
misc_feature           1..56
                       note = Forword primer
source                 1..56
                       mol_type = other DNA
                       organism = synthetic construct
SEQUENCE: 12
ccgtcagatc ctcgagatct gcgatctaag taatgtccaa tttactgacc gtacac      56

SEQ ID NO: 13          moltype = DNA  length = 67
FEATURE                Location/Qualifiers
misc_feature           1..67
                       note = Reverse primer
source                 1..67
                       mol_type = other DNA
                       organism = synthetic construct
SEQUENCE: 13
ataggctagc ctcgaggata tcaagatctg gcctcggcgg ccaatgtcca atttactgac  60
cgtacac                                                           67

SEQ ID NO: 14          moltype = DNA  length = 74
FEATURE                Location/Qualifiers
misc_feature           1..74
                       note = Forward primer
source                 1..74
                       mol_type = other DNA
                       organism = synthetic construct
```

-continued

```
SEQUENCE: 14
atccactagt tctagaataa cttcgtataa tgtatgctat acgaagttat gtcgcggcct  60
tacgccagaa tgcg                                                     74

SEQ ID NO: 15          moltype = DNA  length = 74
FEATURE                Location/Qualifiers
misc_feature           1..74
                       note = Reverse primer
source                 1..74
                       mol_type = other DNA
                       organism = synthetic construct
SEQUENCE: 15
ccgtcagatc ctcgagataa cttcgtatag catacattat acgaagttat atctgcgatc  60
taagtaagct tggc                                                     74
```

NUCLEIC ACID CONSTRUCT SET, KIT, DETECTION METHOD AND METHOD FOR PREDICTING DRUG EFFECT

CROSS-REFERENCE TO RELATED APPLICATIONS

This application is a Continuation Application of PCT Application No. PCT/JP2021/044292, filed Dec. 2, 2021 and based upon and claiming the benefit of priority from Japanese Patent Application No. 2020-201985, filed Dec. 4, 2020, the entire contents of all of which are incorporated herein by reference.

REFERENCE TO A SEQUENCE LISTING

In accordance with 37 CFR § 1.831, the present specification makes reference to a Sequence Listing submitted electronically as a .xml file named "544838US_ST26_102622.xml". The .xml file was generated on Oct. 26, 2022 and is 24,652 bytes in size. The entire contents of the Sequence Listing are hereby incorporated by reference.

FIELD

Embodiments described herein relate generally to a set of nucleic acid constructs, a kit, a detection method, and a method for predicting an effect of a drug.

BACKGROUND

DNA homologous recombination is an important function for repairing damaged DNA. It is known that deficiency in the DNA homologous recombination function occurs in many cancers. For example, breast cancer with a DNA homologous recombination deficiency is a refractory cancer classified as a triple negative type. For early detection and effective treatment of such disease, a method for efficiently detecting cells having the DNA homologous recombination deficiency is required.

BRIEF DESCRIPTION OF THE DRAWINGS

FIG. 1 is a diagram illustrating an example of a set of nucleic acid constructs according to an embodiment.

FIG. 2 is a flowchart describing an example of a detection method according to an embodiment.

FIG. 3 is a diagram illustrating an example of behaviors of the nucleic acid constructs of the embodiment in a cell having a DNA homologous recombination function.

FIG. 4 is a diagram illustrating an example of behaviors of the nucleic acid constructs of the embodiment in a cell having a DNA homologous recombination deficiency.

FIG. 6 is a flowchart describing an example of a method for predicting an effect of a drug of an embodiment.

FIG. 7 is sectional views of lipid particles of an embodiment encapsulating the nucleic acid constructs.

DETAILED DESCRIPTION

Figure 5:
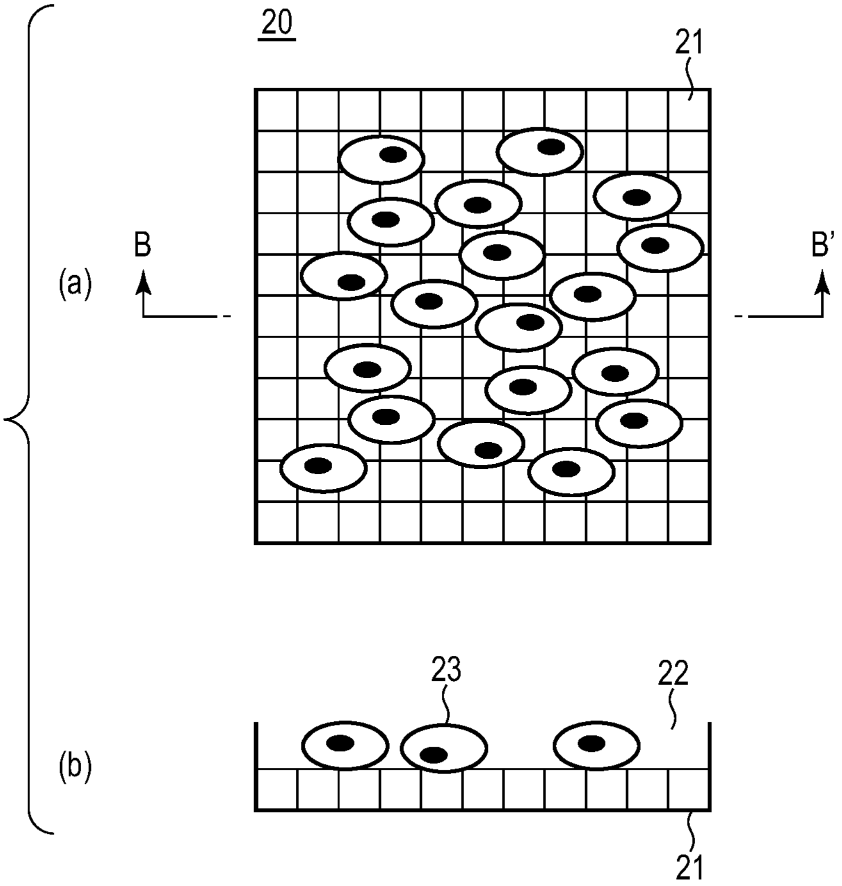
FIG. 5 is a plan view and a sectional view, respectively, illustrating an example of a CMOS image sensor of the embodiment.

In general, according to one embodiment, a set of nucleic acid constructs which detects a DNA homologous recombination deficiency comprises a first nucleic acid construct and a second nucleic acid construct. The first nucleic acid construct includes a first promoter sequence and a cleaved Cre gene ligated to downstream of the first promoter sequence. The second nucleic acid construct includes a second promoter sequence, a first loxP sequence ligated to downstream of the second promoter sequence, a reporter gene ligated to downstream of the first loxP sequence, and a second loxP sequence ligated to downstream of the reporter gene.

Embodiments will be described hereinafter with reference to the accompanying drawings. Note that, in these embodiments, substantially the same structural elements will be designated by the same reference symbols sign and the explanations therefor may be partly omitted. Further, the drawings are only schematic, and therefore, the relation between the thickness of each element and its planar dimension, the ratio in thickness between the elements and the like may be different from those of the actual cases.

Set of Nucleic Acid Constructs

According to an embodiment, a set of nucleic acid constructs used for detecting cells having a DNA homologous recombination (HR) deficiency is provided. The set includes a first nucleic acid construct and a second nucleic acid construct. Although details will be described later, it is possible to detect whether or not cells to be tested (test cells) have the DNA homologous recombination deficiency by transfecting the present set of nucleic acid constructs into the cells.

As shown in part (a) of FIG. 1, the first nucleic acid construct 1 includes a first promoter sequence P1 and a cleaved Cre gene 2 ligated to downstream of the first promoter sequence P1. The first nucleic acid construct 1 can be double-stranded DNA.

As shown in part (b) of FIG. 1, the second nucleic acid construct 10 includes a second promoter sequence P2, a first loxP sequence 11 ligated to downstream of the second promoter sequence P2, a reporter gene 12 ligated to downstream of the first loxP sequence 11, and a second loxP sequence 13 ligated to downstream of the reporter gene 12. The second nucleic acid construct 10 can be double-stranded DNA.

Ligation as used in the specifications includes a case where two sequences are ligated without including another sequence therebetween and a case where two sequences are ligated with an arbitrary sequence included therebetween. The arbitrary sequence is, for example, a spacer sequence. The spacer sequence is a nucleic acid sequence that is different from each of the above sequences and their complementary sequences and is unlikely to affect the activity of these sequences. The sequences are ligated so that each of the function can be operated.

Hereinafter, the sequences included in the nucleic acid constructs will be described in detail.

The first promoter sequence P1 and the second promoter sequence P2 are preferably selected from a virus-derived promoter and a tissue-specific promoter. The virus-derived promoter is, for example, a cytomegalovirus (CMV) promoter, a simian virus 40 (SV40) promoter, a thymidine kinase (TK) promoter, or the like. The tissue-specific promoter is a promoter used specifically in a tissue derived from the test cells. Therefore, the tissue-specific promoter is selected according to the type of the test cells. For example, in a case where the test cells are breast cancer cells, a mammary gland tissue-specific promoter, for example, an estrogen promoter or an estrogen receptor promoter, is preferably used. However, the first promoter sequence P1 and the second promoter sequence P2 are not limited to those described above as long as they have a function of a promoter sequence and may be those obtained by substituting or deleting any base in the base sequence of the promoter sequence described above.

The first promoter sequence P1 and the second promoter sequence P2 may be the same as each other, or may be different from each other.

The cleaved Cre gene 2 is, for example, a Cre gene cleaved at one site. Here, the Cre gene is used in the Cre/loxP system which is a genetic recombination reaction system derived from bacteriophage P1. The Cre gene is a gene encoding a Cre protein and has, for example, a sequence of SEQ ID NO: 1 in Table 1.

TABLE 1

| Cre gene |
|---|
| (SEQ ID NO: 1) |
| ATGTCCAATTTACTGACCGTACACCAAAATTTGCCTGCATTACCGGTCG |
| ATGCAACGAGTGATGAGGTTCGCAAGAACCTCATGGACATGTTCAGGGA |
| TCGCCAGGCGTTTTCTGAGCATACCTGGAAAATGCTTCTGTCCGTTTGC |
| CGGTCGTGGGCGGCATGGTGCAAGTTGAATAACCGGAAATGGTTTCCCG |
| CAGAACCTGAAGATGTTCGCGATTATCTTCTATATCTTCAGGCGCGCGG |
| TCTGGCAGTAAAAACTATCCAGCAACATTTGGGCCAGCTAAACATGCTT |
| CATCGTCGGTCCGGGCTGCCACGACCAAGTGACAGCAATGCTGTTTCAC |
| TGGTTATGCGGCGGATCCGAAAAGAAAACGTTGATGCCGGTGAACGTGG |
| AAAACAGGCTCTAGCGTTCGAACGCACTGATTTCGACCAGGTTCGTTCA |
| CTCATGGAAAATAGCGATCGCTGCCAGGATATACGTAATCTGGCATTTC |
| TGGGGATTGCTTATAACACCCTGTTACGTATAGCCGAAATTGCCAGGAT |
| CAGGGTTAAAGATATCTCACGTACTGACGGTGGGAGAATGTTAATCCAT |
| ATTGGCAGAACGAAAACGCTGGTTAGCACCGCAGGTGTAGAGAAGGCAC |
| TTAGCCTGGGGGTAACTAAACTGGTCGAGCGATGGATTTCCGTCTCTGG |
| TGTAGCTGATGATCCGAATAACTACCTGTTTTGCCGGGTCAGAAAAAAT |
| GGTGTTGCCGCGCCATCTGCCACCAGCCAGCTATCAACTCGCGCCCTGG |
| AAGGGATTTTTGAAGCAACTCATCGATTGATTTACGGCGCTAAGGATGA |
| CTCTGGTCAGAGATACCTGGCCTGGTCTGGACACAGTGCCCGTGTCGGA |
| GCCGCGCGAGATATGGCCCGCGCTGGAGTTTCAATACCGGAGATCATGC |
| AAGCTGGTGGCTGGACCAATGTAAATATTGTCATGAACTATATCCGTAC |
| CCTGGATAGTGAAACAGGGGCAATGGTGCGCCTGCTGGAAGATGGCGAT |
| TAG |

A cleavage site 3 of the cleaved Cre gene 2 has a configuration capable of expressing the Cre protein by being repaired by a DNA homologous recombination function.

For example, at the 5' end of the cleavage site 3, a second sequence 5 having a base sequence homologous to a first sequence 4 which is a portion of the 3'-side end base sequence of the cleavage site 3 is located. The first sequence 4 and the second sequence 5 are arranged in the same direction. The base length of the first sequence 4 and the second sequence 5 are, for example, 3 bases to 120 bases, and preferably 10 bases to 30 bases.

Specific examples of the first sequence 4 and the second sequence 5 will be described with reference to Table 2. In a case where TTATGCGGCG (SEQ ID NO: 2, underlined) in the Cre gene (SEQ ID NO: 1) is selected as the first sequence 4, a base sequence of a 5'-side fragment 6 of the cleaved Cre gene 2 can be the base sequence of SEQ ID NO: 3 in Table 2 (the underlined part is the first sequence 4). Furthermore, a base sequence of a 3'-side fragment 7 can be the base sequence of SEQ ID NO: 4 in Table 2 (the underlined part is the second sequence 5).

TABLE 2

| |
|---|
| Cre gene |
| (SEQ ID NO: 1) |
| ATGTCCAATTTACTGACCGTACACCAAAATTTGCCTGCATTACCGGTCGA |
| TGCAACGAGTGATGAGGTTCGCAAGAACCTGATGGACATGTTCAGGGATC |
| GCCAGGCGTTTTCTGAGCATACCTGGAAAATGCTTCTGTCCGTTTGCCGG |
| TCGTGGGCGGCATGGTGCAAGTTGAATAACCGGAAATGGTTTCCCGCAGA |
| ACCTGAAGATGTTCGCGATTATCTTCTATATCTTCAGGCGCGCGGTCTGG |
| CAGTAAAAACTATCCAGCAACATTTGGGCCAGCTAAACATGCTTCATCGT |
| CGGTCCGGGCTGCCACGACCAAGTGACAGCAATGCTGTTTCACTGG**TTAT** |
| **GCGGCG**GATCCGAAAAGAAAACGTTGATGCCGGTGAACGTGCAAAACAGG |
| CTCTAGCGTTCGAACGCACTGATTTCGACCAGGTTCGTTCACTCATGGAA |
| AATAGCGATCGCTGCCAGGATATACGTAATCTGGCATTTCTGGGGATTGC |
| TTATAACACCCTGTTACGTATAGCCGAAATTGCCAGGATCAGGGTTAAAG |
| ATATCTCACGTACTGACGGTGGGAGAATGTTAATCCATATTGGCAGAACG |
| AAAACGCTGGTTAGCACCGCAGGTGTAGAGAAGGCACTTAGCCTGGGGGT |
| AACTAAACTGGTCGAGCGATGGATTTCCGTCTCTGGTGTAGCTGATGATC |
| CGAATAACTACCTGTTTTGCCGGGTCAGAAAAAATGGTGTTGCCGCGCCA |
| TCTGCCACCAGCGAGCTATCAACTCGCGCCCTGGAAGGGATTTTTGAAGC |
| AACTCATCGATTGATTTACGGCGCTAAGGATGACTCTGGTCAGAGATACC |
| TGGCCTGGTCTGGACACAGTGCCCGTGTCGGAGCCGCGCAGAGATATGGC |
| CCGGCTGGAGTTTCAATACCGGAGATCATGCAAGCTGGTGGCTGGACCAA |
| TGTAAATATTGTCATGAACTATATCCGTACCCTGGATAGTGAAACAGGGG |
| CAATGGTGCGCCTGCTGGAAGATGGCGATTAG |
| 5'-side fragment |
| (SEQ ID NO: 3) |
| ATGTCCAATTTACTGACCGTACACCAAAATTTGCCTGCATTACCGGTCGA |
| TGCAACGAGTGATGAGGTTCGCAAGAACCTGATGGACATGTTCAGGGATC |
| GCCAGGCGTTTTCTGAGCATACCTGGAAAATGCTTCTGTCCGTTTGCCGG |
| TCGTGGGCGGCATGGTGCAAGTTGAATAACCGGAAATGGTTTCCCGCAGA |
| ACCTGAAGATGTTCGCGATTATCTTCTATATCTTCAGGCGCGCGGTCTGG |
| CAGTAAAAACTATCCAGCAACATTTGGGCCAGCTAAACATGCTTCATCGT |
| CGGTCCGGGCTGCCACGACCAAGTGACAGCAATGCTGTTTCACTGG**TTAT** |
| **GCGGCG** |
| 3'-side fragment |
| (SEQ ID NO: 4) |
| **TTATGCGGCG**GATCCGAAAAGAAAACGTTGATGCCGGTGAACGTGCAAAA |
| ACAGGCTCTAGCGTTCGACGCACTGATTTCGACCAGGTTCGTTCACTCAT |
| GGAAAATAGCGATCGCTGCCAGGATATACGTAATCTGGCATTTCTGGGGA |
| TTGCTTATAACACCCTGTTACGTATAGCCGAAATTGCCAGGATCAGGGTT |
| AAAGATATCTCACGTACTGACGGTGGGAGAATGTTAATCCATATTGGCAG |
| AACGAAAACGCTGGTTAGCAGCGCAGGTGTAGAGAAGGCAGTTAGCCTGG |
| GGGTAACTAAACTGGTCGAGCGATGGATTTCCGTCTCTGGTGTAGCTGAT |
| GATCCGAATAACTACCTGTTTTGCCGGGTCAGAAAAAATGGTGTTGCCGC |
| GCCATCTGCCACCAGCCAGCTATCAACTCGCGCCCTGGAAGGGATTTTTG |
| GAAGCAACTCATCATTGATTTACGGCGCTAAGGATGACTCTGGTCAGAGA |
| TACCTGGCCTGGTCTGGACACAGTGCCCGTGTCGGAGCCGCGCGAGATAT |
| GGCCCGCGCTGGAGTTTCAATACCGGAGATCATGCAAGCTGGTGGCTGGA |
| CCAATGTAAATATTGTCATGAACTATATCCGTAACCTGGATAGTGAAACA |
| GGGGCAATGGTGCGCCTGCTGGAAGATGGCGATTAG |

Table 2 shows an example in which the base length of the first sequence 4 and the second sequence 5 are 10 bases, however, in a case where the base length are 20 bases, for example, the sequence TTATGCGGCGGATCCGAAAA (SEQ ID NO: 5) can be selected as the first sequence 4 and second sequence 5. In a case where the base length are 30 bases, for example, the sequence TTATGCGGCG-GATCCGAAAAGAAAACGTTG (SEQ ID NO: 6) can be selected. The position of the cleavage site 3 and the sequence selected as the first sequence 4 and the second sequence 5 are not limited to the above examples, and any location and sequence in the Cre gene may be selected, as long as the Cre gene is inactivated by being cleaved, and the Cre protein is not expressed in such state.

As described above, since the cleavage site 3 contains the first sequence 4 and the second sequence 5, which are homologous sequences, the Cre gene can be formed and expressed by the DNA homologous recombination repair.

The ends of the first sequence 4 and the second sequence 5 on the side of the cleavage site 3 may contain an additional base sequence. For example, a base sequence that remains when the cleaved Cre gene 2 is synthesized, for example, a protruding end of a restriction enzyme site and the like, may be present. Those can be removed during the DNA repair.

The first loxP sequence 11 and the second loxP sequence 13 are sequences that the Cre protein in the Cre/loxP system recognizes to perform recombination therein. Both the first loxP sequence 11 and the second loxP sequence 13 can contain, for example, the base sequences in Table 2 below, however, modified base sequences may be used as long as these have the above-described function of the loxP sequence.

TABLE 3

| loxP sequence (SEQ 1D NO: 7) |
|---|
| ATAACTTCGTATAGCATACATTATACGAAGTTAT |

The first loxP sequence 11 and the second loxP sequence 13 are preferably arranged in the same direction in the second nucleic acid construct 10, however, these may be arranged in the opposite direction to each other.

The reporter gene 12 is, for example, a fluorescent protein gene, a luminescent protein gene, a radical oxygen producing gene, a drug resistance gene, or the like. For example, genes of fluorescent proteins such as a blue fluorescent protein gene, a green fluorescent protein gene, and a red fluorescent protein gene; genes of luminescent enzyme proteins such as a firefly luciferase gene, a *Renilla* luciferase gene, and a NanoLuc (registered trademark) luciferase gene; genes of radical oxygen-generating enzymes such as a xanthine oxidase gene and a nitric oxide synthase gene; drug resistance genes such as a β ampicillin resistance gene, a kanamycin resistance gene, a chloramphenicol resistance gene, a streptomycin resistance gene, a tetracycline resistance gene, a hygromycin resistance gene, a puromycin resistance gene, and a blasticidin resistance gene; heavy metal-binding protein genes, or the like can be used.

However, the reporter gene 12 is not limited to the reporter genes described above and may be another reporter gene or a reporter gene obtained by substituting or deleting any base in the base sequence of the reporter gene described above, as long as it has a function of a reporter.

The reporter gene 12 is preferably, for example, a gene encoding the Nanoluc (registered trademark) luciferase, which is a luciferase. An example of the base sequence of that is shown in Table 4.

TABLE 4

| Gene encoding Nanoluc (registered trademark) |
|---|
| (SEQ ID NO: 8) |
| AGCTTGGCAATCCGGTACTGTTGGTAAAGCCACCATGGTCTTCACACTC |
| GAAGATTTCGTTGGGGACTGGCGACAGACAGCCGGCTACAACCTGGACC |
| AAGTCCTTGAACAGGGAGGTGTGTCCAGTTTGTTTCAGAATCTCGGGCT |

TABLE 4-continued

| Gene encoding Nanoluc (registered trademark) |
|---|
| GTCCGTAACTCCGAICCAAAGGATTGTCCTGAGCGGTGAAAATGGGCTG |
| AAGATCGACATCCATGTCATCATCCCGTATGAAGGTCTGAGCGGCGACC |
| AAATGGGCCAGATCGAAAAAATTTTTAAGGTGGTGTACCCTGTGGATGA |
| TCATCACTTTAAGGTGATCCTGCACTATGGCACACTGGTAATCGACGGG |
| GTTACGCCGAACATGATCGACTATTTCGGACGGCCGTATGAAGGCATCG |
| CCGTGTTCGACGGCAAAAAGATCACTGTAACAGGGACCCTGTGGAACGG |
| CAACAAAATTATCGACGAGCGCCTGATCAACCCCGACGGCTCCCTGCTG |
| TTCCGAGTAACCATCAACGGAGTGACCGGCTGGCGGCTGTGCGAACGCA |
| TTCTGGCGTAA |

A transcription termination sequence may be further ligated to downstream of the cleaved Cre gene 2 in the first nucleic acid construct 1 and downstream of the reporter gene 12 in the second nucleic acid construct 10. The transcription termination sequence is, for example, a poly(A) addition signal sequence of simian virus 40 (SV40), a poly(A) addition signal sequence of a bovine growth hormone gene, an artificially synthesized poly(A) addition signal sequence, or the like. However, the transcription termination sequence is not limited to these, and another sequence, a sequence obtained by modifying the base sequence of the transcription termination sequences described above, or the like may be used, as long as it has a function of a transcription termination sequence.

The first nucleic acid construct 1 and the second nucleic acid construct 10 may be vectors. For example, it may be a vector based on a plasmid vector or a viral vector.

The portion of the cleaved Cre gene 2 in the first nucleic acid construct 1 can be prepared by, for example, as follows. First, a sequence including the 5'-side fragment 6 of the cleaved Cre gene 2, a first restriction enzyme site, an arbitrary sequence, a second restriction enzyme site, and the 3'-side fragment 7 of the cleaved Cre gene 2 is synthesized. Next, a vector which contains the first promoter sequence P1 and serves as a base of the first nucleic acid construct 1 is prepared, and the synthetic DNA obtained as described above is inserted downstream of the first promoter sequence P1 of the base vector. Then, the first restriction enzyme site and the second restriction enzyme site are cleaved with a restriction enzyme, thereby obtaining the first nucleic acid construct having the cleaved Cre gene 2.

The second nucleic acid construct 10 is obtained as follows. First, the reporter gene 12 is prepared, and the first loxP sequence 11 and the second loxP sequence 13 are added to the ends thereof, respectively. For example, by amplifying the reporter gene 12 using a primer containing a loxP sequence, a sequence containing the first loxP sequence 11, the reporter gene 12, and the second loxP sequence 13 can be synthesized. Next, a vector which contains the second promoter sequence P2 and serves as a base of the second nucleic acid construct 10 is prepared, and the synthetic DNA obtained as described above is inserted downstream of the second promoter sequence P2 of the base vector, thereby obtaining the second nucleic acid construct 10.

The first nucleic acid construct 1 and the second nucleic acid construct 10 may contain any base sequence in addition to the above sequences. Such a base sequence may be, for example, a base sequence having a specific function or a sequence not having a function. The base sequence having a function is, for example, an additional reporter gene expression unit, a replication initiation sequence, and/or a replication initiation protein expression unit.

In a further embodiment, there may be a plurality of the cleavage sites 3 in the cleaved Cre gene 2. However, since the efficiency of DNA repair is reduced in this case, the number of the cleavage sites is preferably small, and is more preferably one.

Detection Method for DNA Homologous Recombination Deficiency

According to an embodiment, a detection method for cells having a DNA homologous recombination deficiency using the first nucleic acid construct 1 and the second nucleic acid construct 10 is provided.

The present detection method includes, for example, the following steps described in FIG. 2.

(S1) transfection step of transfecting the first nucleic acid construct and the second nucleic acid construct into test cells, (S2) culture step of culturing the test cells, and (S3) detection step of detecting the activity of the reporter protein expressed from the reporter gene.

Hereinafter, an example of a procedure of each step will be described in detail.

First, test cells are prepared. The test cells can be, for example, cells derived from a human, an animal, or a plant, or cells derived from a microorganism such as bacteria or fungi. The test cells are preferably animal cells, more preferably mammalian cells, and most preferably human cells. The test cells are, for example, cells taken out of the living body, and may be, for example, cells separated from a body fluid such as blood, a tissue, a biopsy, or the like. The test cells are, for example, cancer cells. The cancer cells are preferably, for example, cancer cells obtained from a primary lesion of breast cancer, ovarian cancer, prostate cancer, and/or a cancer in the digestive system, or cancer cells of a lesion to which these cancers have metastasized. The test cells may be, for example, isolated cells, cultured cells, or an established cell line. Alternatively, the cells may be cells in the living body.

Next, the first nucleic acid construct 1 and the second nucleic acid construct 10 are transfected into the test cells (transfection step S1). For example, in a case where the test cells are cells taken out of the living body, transfection step S1 can be performed by a known method such as a liposome method, a lipofection method, an electroporation method, a calcium phosphate co-precipitation method, a cationic polymer method, a microinjection method, a particle gun method, and a sonoporation method.

It is particularly preferable to use the liposome method. In the liposome method, the first nucleic acid construct 1 and the second nucleic acid construct 10 are encapsulated in liposomes (lipid particles), and a composition or the like containing it is brought into contact with the cells. As a result, the lipid particles are taken up into the cells by, for example, endocytosis, and the encapsulated content is released into the cells. Details of the lipid particles are described later in an embodiment of a kit.

In a case where the test cells are the cells in the living body, the transfection can be performed by injection or instillation of the composition containing the first nucleic acid construct 1 and the second nucleic acid construct 10 into the living body. The composition may contain, for example, the lipid particles encapsulating the first nucleic acid construct 1 and the second nucleic acid construct 10.

Next, the test cells are cultured (culture step S2). The culture may be performed by a known method suitable for survival of the test cells, which is selected depending on the type of the test cells. For example, a culture temperature is preferably about 37° C., and a $CO_2$ concentration is preferably about 5%. In addition, the culture is preferably performed for 1 day to 3 days. A medium is a solid medium or a liquid medium, and a medium suitable for the survival of the test cells can be used.

The behavior of each nucleic acid construct in the test cells having a DNA homologous recombination function after transfection step S1 will be described with reference to FIG. 3. Furthermore, the behavior in the cells having the DNA homologous recombination deficiency will be described with reference to FIG. 4.

As shown in FIG. 3, in a test cell having the DNA homologous recombination function, the cleavage site of the cleaved Cre gene 2 in the first nucleic acid construct 1 can be repaired by a DNA homologous recombination activity (HR), thereby forming a Cre gene 2*a* (part (a) of FIG. 3). Thus, a Cre protein 8 can be synthesized by the expression of the Cre gene 2*a* (part (b) of FIG. 3). The Cre protein 8 binds to the first loxP sequence 11 and the second loxP sequence 13 in the second nucleic acid construct 10 (part (c) of FIG. 3) and causes recombination between the two loxP sequences. As a result, the second nucleic acid construct 10 is divided into two circular nucleic acids, and the second promoter sequence P2 and the reporter gene 12 are separated (part (d) of FIG. 3). Consequently, the reporter gene 12 is inactivated, and the expression thereof is reduced or does not take place.

On the other hand, as shown in FIG. 4, in a cell having the DNA homologous recombination deficiency, the cleaved Cre gene 2 in the first nucleic acid construct 1 is not repaired (part (a) of FIG. 4). In this case, since the Cre gene is not expressed, the reporter gene 12 in the second nucleic acid construct 10 is not inactivated, and the reporter gene 12 is expressed, thereby synthesizing a reporter protein 14 (part (b) of FIG. 4). The reporter protein 14 shows a detectable activity according to the type, for example, generation of a signal 15.

The case where the first loxP sequence 11 and the second loxP sequence 13 are arranged in the same direction is described above, and meanwhile, in a case arranged in opposite directions, the direction of the reporter gene 12 is reversed by the recombination between the two loxP sequences after the binding of the Cre protein 8 in part (c) of FIG. 3. This causes the reporter gene 12 to be inactivated.

Next, the activity of the reporter protein 14 is detected (detection step S3). Detection step S3 may be performed in an extract obtained by extracting the reporter protein 14 from the test cells or in a supernatant of a culture solution of the test cells. Alternatively, it can also be performed on the living test cells.

When the reporter protein 14 generates the signal 15, the activity of the reporter gene 12 can be detected by detecting it. The signal 15 is, for example, fluorescence, chemiluminescence, bioluminescence, biochemiluminescence, coloration, or the like, or presentation of molecules such as proteins. The signal 15 can be emitted from the reporter protein 14 itself or can be generated by a reaction, for example, an enzymatic reaction, binding, or the like, between the reporter protein 14 and a specific substance (hereinafter, referred to as "first substance").

In a case where the reporter protein 14 is an enzyme, for example, the first substance is a substrate thereof. For example, in a case where the reporter protein 14 is luciferase, the first substance is luciferin. Alternatively, the signal 15 may be a signal derived from an additional detection reagent (hereinafter, referred to as "second substance") for detecting the presence of a substance generated by the reaction between the reporter protein 14 and the first substance.

For example, in a case where the first substance and/or the second substance is used, these substances can be added to the test cells at the beginning of detection step S3. These substances may be added to the culture medium of the test cells or may be inserted into the cells. Alternatively, it may be added to an extract or a supernatant obtained from the test cells.

The detection of the signal 15 may be performed using any known method selected according to the type thereof.

In a case where the reporter protein 14 is a fluorescent protein, the signal 15 is obtained as fluorescence generated from the fluorescent protein by irradiating the cells with excitation light. The fluorescence (signal 15) can be detected by visual observation, a microscope, a flow cytometer, image analysis software, a fluorometer, or the like.

In the case where the reporter protein 14 is luciferase, the signal 15 is obtained as bioluminescence by adding luciferin. The bioluminescence (signal 15) can be detected by visual observation, a microscope, a flow cytometer, image analysis software, a luminometer, or the like.

In a case where the reporter protein 14 is β-galactosidase, the signal 15 is obtained as absorbance of a cell solution or extract by adding a substrate such as 5-brmo-4-chloro-3-indolyl-β-D-galactopyranoside (X-Gal) or o-nitrophenyl-β-D-galactopyranoside (ONPG). The absorbance (signal 15) can be detected by an absorption spectrometer, a spectrophotometer, a turbidimeter, or the like.

In a case where the reporter protein 14 is nitric oxide synthase or xanthine oxidase, a substrate is added, and generated active oxygen is obtained as the signal 15. The active oxygen (signal 15) can be detected by an electron spin resonance apparatus (ESR apparatus) or the like.

In a case where the reporter protein 14 is a heavy metal-binding protein, a measurable heavy metal is added, and the heavy metal binding to the reporter protein is obtained as the signal 15. The heavy metal can be detected by a magnetic resonance imaging apparatus, a nuclear medicine diagnostic apparatus, an MRI imaging apparatus, or an X-ray computed tomography apparatus.

For example, since the intensity of the signal 15 correlates with the expression level of the reporter protein 14, cells in which the signal 15 is obtained and cells in which the intensity of the signal 15 is higher than a threshold value can be determined to be cells having high activity of the reporter gene 12 and having the DNA homologous recombination deficiency. On the contrary, cells in which the signal 15 is not obtained and cells in which the intensity of the signal 15 is lower than the threshold value can be determined to be cells having the DNA homologous recombination function.

The threshold value can be, for example, a value of the expression level (intensity of the signal 15) of the reporter protein 14, which is obtained when the detection method of the embodiment is performed using cells known to have the DNA homologous recombination deficiency.

In a case where the reporter protein 14 is a drug resistant gene, culture step S2 may be performed by adding a corresponding drug to the medium. In this case, the test cells having the DNA homologous recombination deficiency can survive, and the test cells having the DNA homologous recombination function can die. Therefore, the surviving cells can be determined to be cells having high activity of the reporter gene 12 and having the DNA homologous recombination deficiency.

Alternatively, in detection step S3, the reporter protein 14 may be directly detected or quantified instead of performing the detection of the signal 15, the screening with a drug, or the like. In this case, cells in which the reporter protein 14 is detected, cells in which the quantitative value is higher than a threshold value, cells in which the quantitative value is increased, or cells in which the increase amount of the quantitative value is larger than a threshold value can be determined to be cells having high activity of the reporter gene 12 and having the DNA homologous recombination deficiency.

In this way, the cells having the DNA homologous recombination deficiency can be detected.

Culture step S2 and detection step S3 may be performed on a CMOS image sensor. FIG. 5 illustrates a state when a CMOS image sensor 20 is used. Part (a) of FIG. 5 is a plan view of the CMOS image sensor 20, and part (b) of FIG. 5 is a cross-sectional view taken along the line B-B' of part (a) of FIG. 5. The CMOS image sensor 20 includes a plurality of sensing section 21 arranged in a matrix in a two-dimensional region and a sample storage section 22 provided on the plurality of sensing section 21. Test cells 23 can be cultured in the sample storage section 22. Each sensing section 21 is an optical sensor and can two-dimensionally detect the presence or absence of the test cells 23 on the sensing section 21 and the signal 15 generated from the test cells 23 or the medium.

According to the detection method of the embodiment, it is possible to efficiently visualize and detect the cells having the DNA homologous recombination deficiency in a short period of time.

Method for Predicting Effect of Drug

According to an embodiment, a method for predicting an effect of a drug on a cancer in a subject by using the first nucleic acid construct 1 and the second nucleic acid construct 10 is provided.

The drug is a drug that is effective against a cancer with the DNA homologous recombination deficiency. The drug is, for example, a DNA-damaging anticancer agent such as a platinum preparation such as cisplatin, a topoisomerase inhibitor, or a Poly (ADP-ribose) polymerase (PARP) inhibitor.

The present method includes, for example, the following steps shown in FIG. 6.

(S11) transfection step of transfecting the first nucleic acid construct and the second nucleic acid construct into test cells, (S12) culture step of culturing the test cells, (S13) detection step of detecting a signal from a protein expressed from the reporter gene, (S14) calculation step of calculating an positive rate of cells having the DNA homologous recombination deficiency included in the test cells based on the result of the detecting, and (S15) prediction step of predicting an effect of a drug, which is effective against a cancer with the DNA homologous recombination deficiency, on a cancer in the subject based on the positive rate.

Hereinafter, an example of a procedure of each step will be described in detail.

First, test cells are collected from a subject. The subject is an animal, preferably a human. The test cells are cancer cells. The cancer cells are preferably, for example, cancer cells obtained from a primary lesion of breast cancer, ovarian cancer, prostate cancer, and/or a cancer in the digestive system, or cancer cells of a lesion to which these cancers have metastasized. The cancer cells can be collected from a cancer lesion in the subject by biopsy or the like. The test cells may be cultured after the collection.

Transfection step S11 to detection step S13 can be performed in the same manner as transfection step S1 to detection step S3.

Next, the positive rate of the cells having the DNA homologous recombination deficiency is calculated based on the result of detection step S12 (calculation step S14). The positive rate of the cells having the DNA homologous recombination deficiency is obtained by counting the number of the test cells (A) and the number of the cells having the DNA homologous recombination deficiency (B) and substituting the values into Equation (I) below.

$$\text{Positive rate of cells having DNA homologous recombination deficiency}=(B)/(A) \quad \text{Equation (I)}$$

Counting the number of the cells may be performed by a known method. For example, it may be counted visually by microscopic observation or may be automatically counted from a microscopic image. Alternatively, flow cytometry may be used.

The number of the cells (B) is the number of cells having high activity of the reporter gene 12 in detection step S12. For example, the number of the cells (B) is the number of cells from which the signal 15 is obtained. In a case where a drug resistance gene is used as the reporter gene 12, the number of the cells (B) is the number of surviving cells.

The number of the test cells (A) is, for example, the number of cells detected by irradiating the test cells with scattered light. In a case where the drug resistance gene is used, the number of the test cells (A) may be counted before transfection step S11.

Calculation step S14 does not need to be performed on all of the test cells and may be performed on a part of the test cells by sampling or on a part of the test cells in a visual field of the microscope, and the positive rate of the cells having the DNA homologous recombination deficiency in the entire test cells may be estimated from the result.

Next, the effect of the drug on the cancer in the subject is predicted from the positive rate of the cells having the DNA homologous recombination deficiency obtained in calculation step S14. The effect of the drug can be determined to be high in a case where the positive rate of the cells having the DNA homologous recombination deficiency is higher. On the contrary, the effect of the drug can be determined to be low in a case where the positive rate of the cells having the DNA homologous recombination deficiency is lower.

The effect of the drug may be predicted on the basis of a threshold value of the positive rate. For example, when the threshold value of the positive rate is about 40%, and the positive rate is higher than this value, it is possible to determine that the drug is effective. The threshold value may be determined, for example, from past knowledge such as literature. Alternatively, it may be determined by calculating the positive rate of the cells having the DNA homologous recombination deficiency in a cell group in which the effect of the drug is known by performing the method of the embodiment.

Alternatively, from the positive rate, it is also possible to determine the schedule of treatment using the present drug. For example, the dose or administration frequency of the drug may be changed according to the positive rate.

As described above, according to the method for predicting an effect of a drug of the embodiment, the effect of the drug on the cancer in the subject can be efficiently predicted in a short period of time.

Kit

According to an embodiment, a reagent kit used for detecting cells having a DNA homologous recombination deficiency or predicting an effect of a drug on a cancer in a subject is provided.

The kit includes a set of nucleic acid constructs including a first nucleic acid construct and a second nucleic acid construct.

The set of nucleic acid constructs is provided, for example, as a composition contained in a solvent. As the solvent, for example, endotoxin-free water, PBS, TE buffer, HEPES buffer, or the like can be used. The composition may further contain an excipient, a stabilizer, a diluent, and/or an auxiliary agent.

The set of nucleic acid constructs is preferably included in the kit in a state of being encapsulated in lipid particles. The lipid particles will be described with reference to FIG. 7. As shown in FIG. 6, lipid particles 30 are hollow spherical lipid membranes. For example, as shown in part (a) of FIG. 7, the first nucleic acid construct 1 and the second nucleic acid construct 10 are encapsulated together in a single lipid particle 30. Alternatively, as shown in part (b) of FIG. 7, the first nucleic acid construct 1 and the second nucleic acid construct 10 are encapsulated in separate lipid particles 30.

The lipid membrane that constitutes the lipid particles 30 is a lipid membrane such as a monolayer, a lipid bilayer, and a lipid triple layer. In addition, the lipid particles 30 may be a multilayer structure in which a plurality of lipid membranes are further overlapped.

The lipid particles 30 may be composed of one type of lipid material, but is preferably composed of a plurality of types of lipid materials. The lipid material preferably contains, for example, at least a base lipid, a first lipid compound, and a second lipid compound, of which examples are provided below.

The base lipid is preferably a phospholipid or a sphingolipid such as diacylphosphatidylcholine, diacylphosphatidylethanolamine, ceramide, sphingomyelin, dihydrosphingomyelin, cephalin, and cerebroside, or a combination thereof. The base lipid may be, for example, a lipid which is a main component of a biological membrane or may be an artificially synthesized lipid.

It is particularly preferable that a cationic lipid or neutral lipid is used as the base lipid, and the acid dissociation constant of the lipid particles 30 can be adjusted by the content thereof. It is preferable that 1,2-dioleoyl-3-trimethylammonium propane (DOTAP) is used as the cationic lipid, and it is preferable that 1,2-dioleoyl-sn-glycero-3-phosphoethanolamine (DOPE) is used as the neutral lipid.

The base lipid is preferably contained at 30% to about 80% (molar ratio) with respect to the total lipid material. Alternatively, nearly 100% of that may be constituted from the base lipid.

The first lipid compound and the second lipid compound are biodegradable lipids. The first lipid compound can be represented by the formula $Q\text{-}CHR_2$ (In the formula, Q is a nitrogen-containing aliphatic group which contains two or more tertiary nitrogens and no oxygen, Rs are each independently a $C_{12}$ to $C_{24}$ aliphatic group, and at least one R contains a linking group LR selected from the group consisting of —C(═O)—O—, —O—C(═O)—, —O—C (═O)—O—, —S—C(═O)—, —C(═O)—S—, —C(═O)—NH—, and —NHC(═O)— in the main chain or side chain thereof).

In a case where the lipid particles 30 contain the first lipid compound, the surfaces of the lipid particles 30 are non-cationic, therefore, interference with the transfection of the particles into the cell is reduced, and the efficiency of transfecting the encapsulated content can be enhanced.

As the first lipid compound, for example, a lipid having a structure represented by the following formula is preferably used, since the transfection efficiency is more excellent. It is particularly preferable to use a lipid compound of Formula (1-01) and/or a lipid compound of Formula (1-02), shown below.

(1-01)

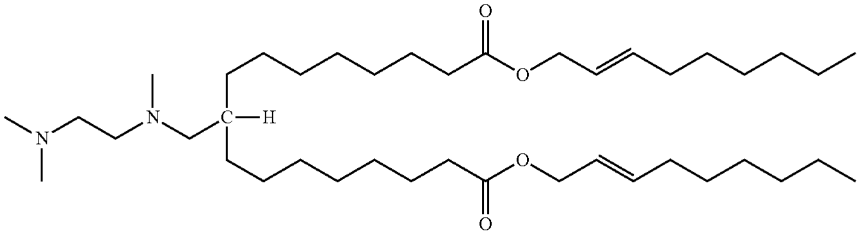

(1-02)

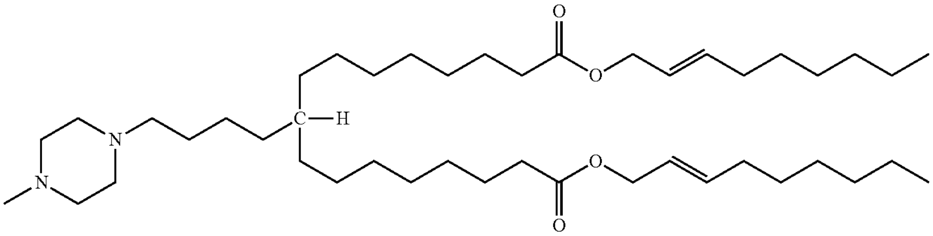

The second lipid compound can be represented by the formula P—[X—W—Y—W'—Z]$_2$ (In the formula, P is an alkyleneoxy having one or more ether bonds in the main chain thereof, Xs are each independently a divalent linking group that includes a tertiary amine structure, Ws are each independently a $C_1$ to $C_6$ alkylene, Ys are each independently a divalent linking group selected from the group consisting of a single bond, an ether bond, a carboxylic acid ester bond, a thiocarboxylic acid ester bond, a thioester bond, an amide bond, a carbamate bond, and a urea bond, W's are each independently a single bond or a $C_1$ to $C_6$ alkylene, and Zs are each independently a fat-soluble vitamin residue, a sterol residue, or a $C_{12}$ to $C_{22}$ aliphatic hydrocarbon group).

In a case where it contains the second lipid compound, the encapsulation amount of the nucleic acid construct in the lipid particles 30 can be increased.

For example, it is preferable to use the second lipid compound having the following structure, since the encapsulation amount of the nucleic acid construct is more excellent. It is particularly preferable to use a compound of Formula (2-01) shown below.

(2-01)

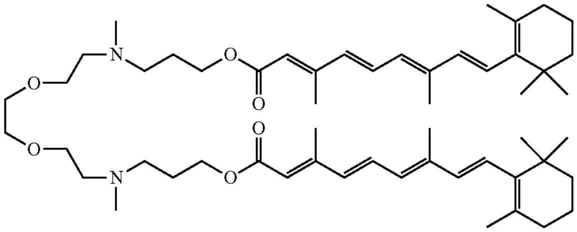

When the lipid particles 30 containing the first and second lipid compounds described above are used, it is possible to increase the encapsulation amount of the nucleic acid construct and to increase the efficiency of transfecting the nucleic acid construct into the test cells. Furthermore, cell death of the test cells into which it is inserted can also be decreased.

The first and second lipid compounds are preferably contained at about 20% to about 70% (molar ratio) with respect to the total lipid material.

It is also preferable that the lipid material contains a lipid that prevents aggregation of the lipid particles 30, such as polyethylene glycol (PEG) dimyristoyl glycerol (DMG-PEG). Such lipid is preferably contained at about 1% to about 5% (molar ratio) with respect to the total lipid material of the lipid particle 30.

The lipid material may further contain a lipid such as a lipid that is relatively less toxic for modulating toxicity; a lipid having a functional group for binding a ligand to the lipid particles 30; and a lipid for suppressing leakage of the encapsulated content, such as sterol including cholesterol. It is particularly preferable to contain cholesterol.

The type and composition of the lipid to be used are appropriately selected in consideration of the intended acid dissociation constant (pKa) of the lipid particles 30, or the size, the type of the encapsulated content and stability in the test cells into which the lipid particles are transfected and the like, of the lipid particles 30.

For example, the lipid particles 30 preferably contain a compound of Formula (1-01) or Formula (1-02) and/or a compound of Formula (2-01), DOPE and/or DOTAP, cholesterol, and DMG-PEG.

The lipid particles 30 can be produced by using a known method used when encapsulating a small molecule in the lipid particles 30, for example, the Bangham method, an organic solvent extraction method, a surfactant removal method, a freeze-thaw method, or the like. For example, a lipid mixture obtained by adding the material of the lipid particles 30 to an organic solvent such as alcohol at a desired ratio and an aqueous buffer containing a component to be encapsulated such as a vector are prepared, and the aqueous buffer is added to the lipid mixture. A mixture thus obtained is stirred and suspended to form the lipid particles 30 in which the vector and the like are encapsulated.

In addition, the kit may further include a reagent for detecting the reporter protein 14. The reagent is, for example, the first substance and/or the second substance described in detection step S3.

The set of nucleic acid constructs and the reagent are provided by being contained in a container individually or in combination with any components.

EXAMPLES

Hereinafter, examples of producing and using the set of nucleic acid constructs of the embodiments will be described.

Example 1. Preparation of Vectors 1 for Detecting Cells Having DNA Homologous Recombination Deficiency A vector A in which an ampicillin resistance gene sequence, a ColE1 origin sequence, an SV40 origin sequence, an SV40 polyA sequence, a CMV promoter sequence, and a BGH polyA sequence were ligated was prepared. After performing restriction enzyme treatment at the XhoI site and the XbaI site downstream of the CMV promoter, 0.8% agarose electrophoresis was performed, and the gel was cut out to purify the cut vector A.

Three types of sequences shown in Tables 5 to 7 below were synthesized. These three types of sequences are a sequence in which homologous sequences of 10 bases are provided at both ends of the Cre gene cleavage site (restriction enzyme site), a sequence in which homologous sequences of 20 bases are provided at both ends of the Cre gene cleavage site, and a sequence in which homologous sequences of 30 bases are provided at both ends of the Cre gene cleavage site. Restriction enzyme sites GGGCCC (ApaI) and GCTAGC (NheI) are provided between the underlined homologous sequences.

TABLE 5

Sequence in which homologous sequences
of 10 bases are provided (SEQ ID NO: 9)
AGTGAACCGTCAGATCCTCGAGatctgcgatctaagtaATGTCCAATTT

ACTGACCGTACACCAAAATTTGCCTGCATTACCGGTCGATGCAACGAGT

TABLE 5-continued

Sequence in which homologous sequences
of 10 bases are provided

GATGAGGTTCGCAAGAACCTGATGGACATGTTCAGGGATCGCCAGGCGT

TTTCTGAGCATACCTGGAAAATGCTTCTGTCCGTTTGCCGGTCGTGGGC

GGCATGGTGCAAGTTGAATAACCGGAAATGGTTTCCCGCAGAACCTGAA

GATGTTCGCGATTATCTTCTATATCTTCAGGCGCGCGGTCTGGCAGTAA

AAACTATCCAGCAACATTTGGGCCAGCTAAACATGCTTCATCGTCGGTC

CGGGCTGCCACGACCAAGTGACAGCAATGCTGTTTCACTGGTTATGCGG

CGGGGCCCGTTAACGCTAGCTTATGCGGCGGATCCGAAAAGAAAACGTT

GATGCCGGTGAACGTGCAAAACAGGCTCTAGCGTTCGAACGCACTGATT

TCGACCAGGTTCGTTCACTCATGGAAAATAGCGATCGCTGCCAGGATAT

ACGTAATCTGGCATTTCTGGGGATTGCTTATAACACCCTGTTACGTATA

GCCGAAATTGCCAGGATCAGGGTTAAAGATATCTCACGTACTGACGGTG

GGAGAATGTTAATCCATATTGGCAGAACGAAAACGCTGGTTAGOACCGC

AGGTGTAGAGAAGGCACTTAGCCTGGGGGTAACTAAACTGGTCGAGCGA

TGGATTTCCGTCTCTGGTGTAGCTGATGATCCGAATAACTACCTGTTTT

GCCGGGTCAGAAAAAATGGTGTTGCCGCGCCATCTGCCACCAGCCAGCT

ATCAACTCGCGCCCTGGAAGGGATTTTTGAAGCAACTCATCGATTGATT

TACGGCGCTAAGGATGACTCTGGTCAGAGATACCTGGCCTGGTCTGGAC

ACAGTGCCCGTGTCGGAGCCGCGCGAGATATGGCCCGCGCTGGAGTTTC

AATACCGGAGATCATGCAAGCTGGTGGCTGGACCAATGTAAATATTGTC

ATGAACTATATCCGTAACCTGGATAGTGAAACAGGGGCAATGGTGCGCC

TGCTGGAAGATGGCGATTAGGGCCGCGACTctagaactagtggatcccc c

TABLE 6

Sequence in which homologous sequences
of 20 bases are provided (SEQ ID NO: 10)
AGTGAACCGTCAGATCCTCGAGatctgcgatctaagtaATGTCCAATTTA

CTGACCGTACACCAAAATTTGCCTGCATTACCGGTCGATGCAACGAGTGA

TGAGGTTCGCAAGAACCTGATGGACATGTTCAGGGATCGCCAGGCGTTTT

CTGAGCATACCTGGAAAATGCTTCTGTCCGTTTGCCGGTCGTGGGCGGCA

TGGTGCAAGTTGAATAACCGGAAATGGTTTCCCGCAGAACCTGAAGATGT

TCGCGATTATCTTCTATATCTTCAGGCGCGCGGTCTGGCAGTAAAAACTA

TCCAGCAACATTTGGGCCAGCTAAACATGCTTCATCGTCGGTCCGGGCTG

CCACGACCAAGTGACAGCAATGCTGTTTCACTGGTTATGCGGCGGATCCG

AAAAGGGCCCGTTAACGCTAGCTTATGCGGCGGATCCGAAAAGAAAACGT

TGATGCCGGTGAACGTGCAAAACAGGCTCTAGCGTTCGAACGCACTGATT

TCGACCAGGTTCGTTCACTCATGGAAAATAGCGATCGCTGCCAGAGTATA

CGTAATCTGGCATTTCTGGGGATTGCTTATAACACCCTGTTACGTATAGC

TABLE 6-continued

| Sequence in which homologous sequences of 20 bases are provided |
|---|
| CGAAATTGCCAGGATCAGGGTTAAAGATATCTCACGTACTGACGGTGGGA |
| GAATGTTAATCCATATTGGCAGAACGAAAACGCTGGTTAGCACCGCAGGT |
| GTAGAGAAGGCACTTAGCCTGGGGGTAACTAAACTOGTCGAGCGATGGAT |
| TTCCGTCTCTGGTGTAGCTGATGATCCGAATAACTACCTGTTTTGCCGGG |
| TCAGAAAAAATGGTGTTGCCGCGCCATCTGCCACCAGCCAGCTATCAACT |
| GCGCGCCCTGAAGGGATTTTTGAAGCAACTCATCGATTGATTTACGGCGC |
| TAAGGATGACTCTGGTCAGAGATACCTGGCCTGGTCTGGACACAGTGCCC |
| AGTGTCGGAGCCGCOCGAGATATGGCCCGCGCTGGAGTTTCATACCGGAG |
| ATCATGCAAGCTGGTGGCTGGACCAATGTAAATATTGTCATGAACTATAT |
| CCGTAACCTGGATAGTGAAACAGGGGCAATGGTGCGCCTGCTGGAAGATG |
| GCGATTAGGGCCGCGACTctagaactagtggatccccc |

TABLE 7

| Sequence in which homologous sequences of 30 bases are provided |
|---|
| (SEQ ID NO: 11) |
| AGTGAACCGTCAGATCCTCGAbatctgcgatctaagtaATGTCCAATTTA |
| CTGACCGTACACCAAAATTTGCCTGCATTACCGGTCGATGCAACGAGTGA |
| TGAGGTTCGCAAGAACCTGATGGACATGTTCAGGGATCGCCAGGCGTTTT |
| CTGAGCATACCTGGAAAATGCTTCTGTCCGTTTGCCGGTCGTGGGCGGCA |
| TGGTGCAAGTTGAATAACCGGAAATGGTTTCCCGCAGAACCTGAAGATGT |
| TCGCGATTATCTTCTATATCTTCAGGCGCGCGGTCTGGCAGTAAAAACTA |
| TCCAGCAACATTTGGGCCAGCTAAACATGCTTCATCGTCGGTCCGGGCTG |
| CCACGACCAAGTGACAGCAATGCTGTTTCACTGGT**TATGCGGCGGATCCG** |
| **AAAAGAAAACGTTG**GGGCCCGTTAACGCTAGCT**TATGCGGCGGATCCGAA** |
| **AAGAAAACGTTG**ATGCCGGTGAACGTGCAAAACAGGCTCTAGCGTTCGAA |
| CGCACTGATTTCGACCAGGTTCGTTCACTCATGGAAAATAGCGATCGCTG |
| CCAGGATATACGTAATCTGGCATTTCTGGGGATTGCTTATAACACCCTGT |
| TACGTATAGCCGAAATTGCCAGGATCAGGGTTAAAGATATCTCACGTACT |
| GACGGTGGGAGAATGTTAATCCATATTGGCAGAACGAAAACGCTGGTTAG |
| CACCGCAGGTGTAGAGAAGGCACTTAGCCTGGGGGTAACTAAACTGGTCG |
| AGCGATTGGATTTCGTCTCTGGTGTAGCTGATGATCCGAATAACTACCTG |
| TTTTGCCGGGTCAGAAAAAATGGTGTTGCCGCGCCATCTGCCACCAGCCA |
| GCTATCAACTCGCGCCCTGGAAGGGATTTTTGAAGCAACTCATCGATTGA |
| TTTACGGCGCTAAGGATGACTCTGGTCAGAGATACCTGGCCTGGTCTGGA |
| CACAGTGCCCGTGTCGGAGCCGCGCGAGATATGGCCCGCGCTGGAGTTTC |
| AATACCGGAGATCATGCAAGCTGGTGGCTGGACCAATGTAAATATTGTCA |
| TGAACTATATCCGTAACCTGGATAGTGAAACAGGGGCAATGGTGCGCCTG |
| CTGGAAGATGGCGATTAGGGCCGCGACTctagaactagtggatccccc |

Each of the three sequences of Tables 5 to 7, as a template, was amplified by performing PCR using the primers of Table 3 under the conditions of Table 9.

TABLE 8

| Primer name | SEQ ID NO | Sequence |
|---|---|---|
| CMV2_Cre_inf_F | 12 | CCGTCAGATCCTCGAGatctgcgatctaagtaatgtccaatttactgaccgtacac |
| CMV2_Cre_inf_R | 13 | ATAGGCTAGCCTCGAGGATATCAAGATCTGGCCTCGGCGGCCAatgtccaatttactgaccgtacac |

TABLE 9

| PCR amplification conditions | | |
|---|---|---|
| 98° C. | 3 min | |
| 98° C. | 10 sec | |
| 60° C. | 15 sec | 35 cycle |
| 68° C. | 1 min | |
| 68° C. | 10 min | |
| 4° C. | ∞ | |

Figure 8:
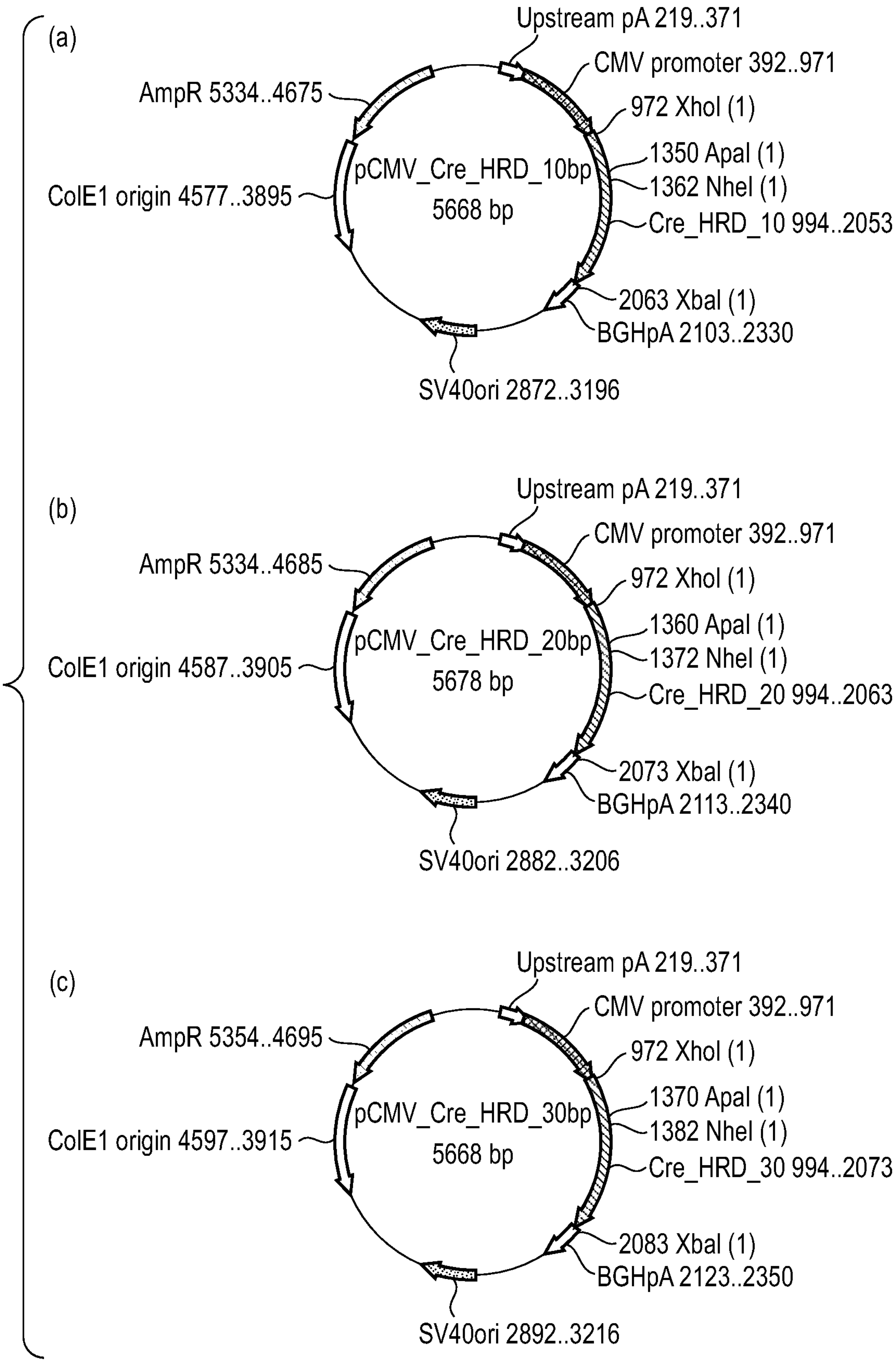
FIG. 8 is a diagram illustrating a vector 1-10, a vector 1-20, and a vector 1-30 prepared in Example 1.

The amplified DNA was purified by 0.8% agarose electrophoresis, and these sequences were ligated to the XhoI/XbaI site of the vector A by using a cloning kit (In-Fusion (registered trademark), Takara). As a result, vectors shown in part (a), (b) and (c) FIG. 8 were obtained. The vectors thus prepared were subjected to DNA sequence analysis to confirm that the vectors is the intended sequences in which the base sequences of Tables 5 to 7 above were inserted into the XhoI/XbaI site of the vector A.

Next, the vectors into which the sequences of Tables 5 to 7 were inserted were each subjected to restriction enzyme treatment with ApaI and NheI, and then subjected to 0.8% agarose electrophoresis and cut out to perform purification. As a result, a vector 1-10 derived from the sequence of Table 5, a vector 1-20 derived from the sequence of Table 6, and a vector 1-30 derived from the sequence of Table 7 were obtained.

Example 2. Preparation of Vector 2 for Detecting Cells Having DNA Homologous Recombination Deficiency A vector A in which an ampicillin resistance gene sequence, a ColE1 origin sequence, an SV40 origin sequence, an SV40 polyA sequence, a CMV promoter sequence, and a BGH polyA sequence were linked was prepared. After performing restriction enzyme treatment on the XhoI site and the XbaI site downstream of the CMV promoter, 0.8% agarose electrophoresis was performed, and the gel was cut out to purify the cut vector A.

The sequence (SEQ ID NO: 8) of the gene of NanoLuc (registered trademark), which is luciferase, as a template, was amplified by performing PCR using primers shown in Table 10 which contain the loxP sequence (SEQ ID NO: 7, underlined) under the conditions of Table 9.

TABLE 10

| Primer name | SEQ ID NO | Sequence |
|---|---|---|
| loxP_nLuc_inf_R | 14 | ATCCACTAGTTCTAGA**ATAACTTCGTATAATGTATGCTATACGAAGTTAT**GTCGCGGCCTTACGCCAGAATGCG |
| loxP2_nLuc_inf_F | 15 | CCGTCAGATCCTCGAG**ATAACTTCGTATAGCATACATTATACGAAGTTAT**atctgcgatctaagtaAGCTTGGC |

Figure 9:
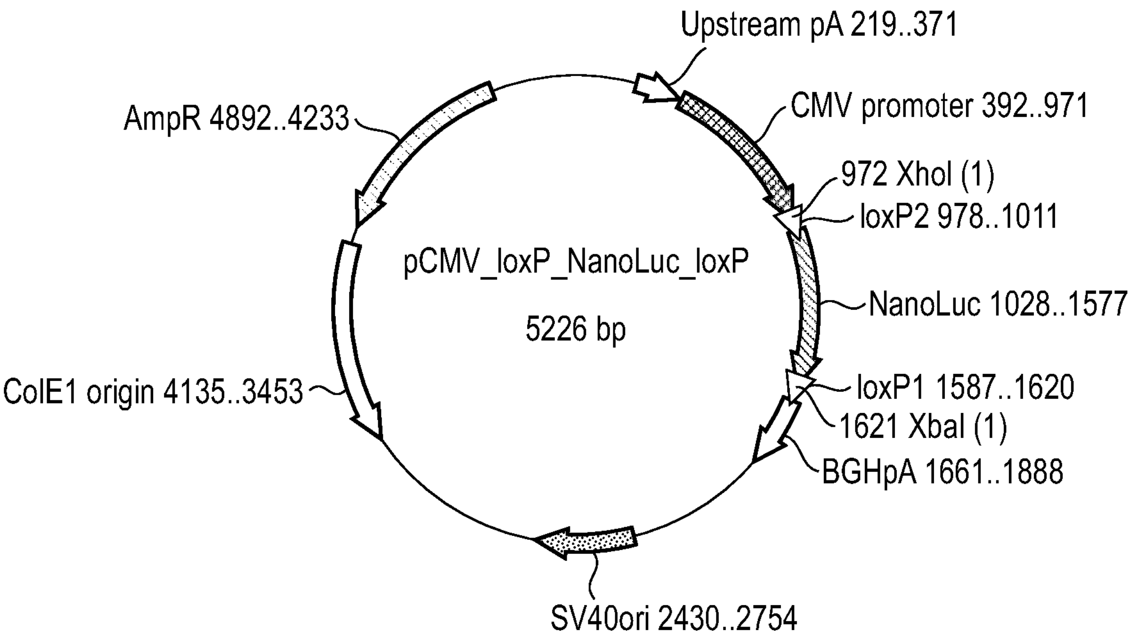
FIG. 9 is a diagram illustrating a vector 2 prepared in Example 2.

The amplified DNA was purified by 0.8% agarose electrophoresis, and the sequence was ligated to the XhoI/XbaI site of the vector A by using a cloning kit (In-Fusion (registered trademark), Takara). As a result, a reporter vector shown in FIG. 9 was obtained. The vector thus prepared was subjected to DNA sequence analysis to confirm that the vector is the intended sequence in which the reporter gene (SEQ ID NO: 8) which was interposed between the loxP sequences (SEQ ID NO: 7) was inserted into the XhoI/XbaI site of the vector A. This vector was defined as a vector 2.

Example 3. Preparation of Lipid Particles Encapsulating Vectors 1 and Vector 2

A cationic peptide was added to a DNA solution containing each of the vector 1-10, the vector 1-20, and the vector 1-30 prepared in Example 1 and the vector 2 prepared in Example 2 to form DNA-peptide condensates. Next, it was added to solutions obtained by dissolving lipids (FFT 10 (lipid compound of Formula (1-01))/SST04 (lipid compound of Formula (2-01))/DOTAP/DOPE/cholesterol/PEG-DMG=37/15/10.5/10.5/30/2 mol) in ethanol. To the mixtures thus obtained, 10 mM HEPES (pH 7.3) was gently added, and then it was washed and concentrated by centrifugal ultrafiltration to obtain lipid particles encapsulating the vector 1-10, the vector 1-20, and the vector 1-30, respectively, and lipid particles encapsulating the vector 2. The DNA encapsulation amount in the lipid particles was measured with a DNA quantification kit (Quant-iT™ PicoGreen™ dsDNA Assay Kit manufactured by Thermo Fisher Scientific).

Example 4. Transfection of Vectors 1 and Vector 2 Into Cell Line

Transfection into Human Mammary Tumor-Derived Cell Line

A human mammary tumor-derived cell line (MCF-7) was subjected to adhesion culture at 37° C. in a 5% $CO_2$ atmosphere in a culture flask using a medium (MEM, GIBCO) to which 10% fetal bovine serum (FBS) was added. After the culture, the medium was removed, and the cells were washed with PBS, and then the cells were detached by 0.25% trypsin-EDTA treatment. Then, the cells were suspended in a medium to which 10% FBS was added to inactivate trypsin. After recovering the cells by centrifugation, the cells were suspended in a medium to which 10% FBS was added to be $2.0\times10^5$ cells/mL. To a 96 well culture dish (manufactured by Thermo Fisher Scientific), 200 µL of the cell suspension was added to be $4.0\times10^4$ cells/well.

Next, the lipid particles encapsulating the three types of vectors 1 prepared in Example 3 were added to the wells to be a DNA concentration of 50 ng/well. At the same time, the lipid particles encapsulating the vector 2 prepared in Example 3 were further added to the wells to be a DNA concentration of 1 ng/well. As a control, a well to which only the vector 2 was added was also provided. Therefore, a sample to which only the vector 2 was added, a sample to which the vector 1-10 and the vector 2 were added, a sample to which the vector 1-20 and the vector 2 were added, and a sample to which the vector 1-30 and the vector 2 were added were obtained. After the addition, the cells were cultured at 37° C. in a 5% $CO_2$ atmosphere.

Measurement of NanoLuc (Registered Trademark) Expression Level (NanoLuc (Registered Trademark) Luminescence Assay)

48 hours after the addition of the lipid particles, the culture plate was taken out of the incubator, and the medium was removed. Then, the cells were washed with PBS, Glo Lysis Buffer (Promega) was added thereto at 100 µL/well, and the resulting mixtures were frozen at −80° C. for 30 minutes. The mixtures were melted at room temperature and then collected in 1.5 ml centrifuge tubes. The cell lysates were centrifuged at 15,000 rpm for 10 minutes to precipitate cell residues, and 25 µL of supernatant was dispensed into a 96 well plate (Black, Nunc). To the dispensed supernatant, 25 µL of a luciferase substrate solution contained in a luciferase assay system (Nano-Glo (registered trademark) Luciferase Assay System, Promega Corporation) was added and mixed. The luminescence amount of the resulting mixture per 1 well per 0.1 seconds was measured by using a luminometer (Mithras LB 940, Berthold).

Comparative Results of Promoter Activities

Figure 10:
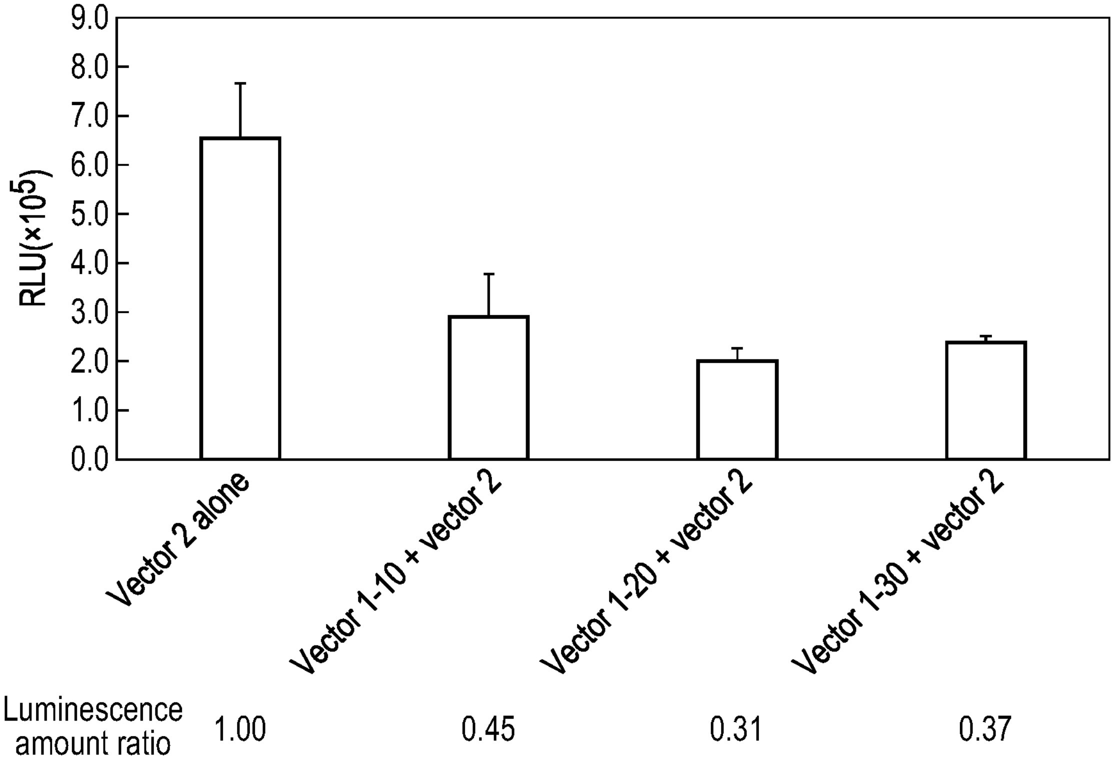
FIG. 10 is a graph showing experimental results in Example 4.

FIG. 10 shows results of measuring the intensities of NanoLuc (registered trademark) luminescence (RLU) resulting from the lipid particles encapsulating the vectors 1 and the vector 2. In the case of adding the vector 2 alone, the value of the luminescence intensity RLU was about $6.5\times10^5$. On the other hand, in the case of transfecting the vector 1-10, the vector 1-20, or the vector 1-30 together, the luminescence intensities RLU were about $2.9\times10^5$ (luminescence amount ratio when the luminescence intensity in the case of adding the vector 2 alone was assumed to be 1:0. 45), $2.0\times10^5$ (luminescence amount ratio: 0.31), and $2.4\times10^5$ (luminescence amount ratio: 0.37), respectively, and were decreased as compared with the case of adding the vector 2 alone.

Such results suggest that in MCF7, which is a breast cancer cell line having a homologous recombination activity, when the vectors 1 were present, the vectors 1 were repaired by the homologous recombination activity, the Cre gene was expressed in the vectors 1, and the Cre protein performed recombination between the loxP sequence portions of vector 2, thereby suppressing the expression of the NanoLuc (registered trademark) gene, which was a reporter. From this, it is possible to expect that the NanoLuc (registered trademark) luminescence intensity (RLU) is maintained in cells with the homologous recombination deficiency (HRD) since the vectors 1 are not repaired, and it is obvious that the cells with the homologous recombination deficiency (HRD) can be detected.

It has become clear that the detection is possible in the same manner in all of the cases where the lengths of the DNA homologous sequences are 10 bases, 20 bases, and 30 bases.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A set of nucleic acid constructs which detect a DNA homologous recombination deficiency, the set comprising: a first nucleic acid construct comprising a first promoter sequence and a cleaved Cre gene ligated to downstream of the first promoter sequence; and a second nucleic acid construct comprising a second promoter sequence, a first loxP sequence ligated to downstream of the second promoter sequence, a reporter gene ligated to downstream of the first loxP sequence, and a second loxP sequence ligated to downstream of the reporter gene, wherein the cleaved Cre gene is composed of two Cre gene fragments obtained by cleaving the Cre gene into two parts without deletion of the base sequence of the Cre gene so as to be inactivated, and of the two Cre gene fragments, an upstream gene fragment of the Cre gene is linked downstream of the first promoter sequence, and a downstream gene fragment of the Cre gene is linked upstream of the first promoter sequence, where in the 5' end of the upstream gene fragment of the Cre gene is linked to a second sequence having a base sequence identical to a portion of the 3' end of the downstream gene fragment of the Cre gene, which is the first sequence, and wherein homologous recombination of the first and second sequences results in a functional Cre gene.

2. The set according to claim 1, wherein a base length of the first sequence and the second sequence are 3 bases to 120 bases.

3. The set according to claim 1, wherein the first sequence and the second sequence are selected from the group consisting of the base sequences of SEQ ID NOs: 2, 5, and 6.

4. The set according to claim 1, wherein the reporter gene is a fluorescent protein gene, a luminescent protein gene, a radical oxygen producing gene, or a drug resistance gene.

5. The set according to claim 1, wherein the first promoter sequence and the second promoter sequence are a virus-derived promoter or a mammary gland tissue-specific promoter.

6. A kit for detecting a DNA homologous recombination deficiency, the kit comprising: lipid particles; a first nucleic acid construct encapsulated in the lipid particles, the first nucleic acid construct including a first promoter sequence and a cleaved Cre gene ligated to downstream of the first promoter sequence; and a second nucleic acid construct encapsulated in the lipid particles, the second nucleic acid construct including a second promoter sequence, a first loxP sequence ligated to downstream of the second promoter sequence, a reporter gene ligated to downstream of the first loxP sequence, and a second loxP sequence ligated to downstream of the reporter gene, wherein the cleaved Cre gene is composed of two Cre gene fragments obtained by cleaving the Cre gene into two parts without deletion of the base sequence of the Cre gene so as to be inactivated, and of the two Cre gene fragments, an upstream gene fragment of the Cre gene is linked downstream of the first promoter sequence, and a downstream gene fragment of the Cre gene is linked upstream of the first promoter sequence, wherein the 5' end of the upstream gene fragment of the Cre gene is linked to a second sequence having a base sequence identical to a portion of the 3' end of the downstream gene fragment of the Cre gene, which is the first sequence, and where in homologous recombination of the first and second sequences results in a functional Cre gene.

7. The kit according to claim 6, wherein a base length of the first sequence and the second sequence are from 3 bases to 120 bases.

8. The kit according to claim 6, wherein the lipid particles comprise, as a material thereof, a compound of the following formula (1-01), a compound of the following formula (1-02), and/or a compound of the following formula (2-01):

(1-01)

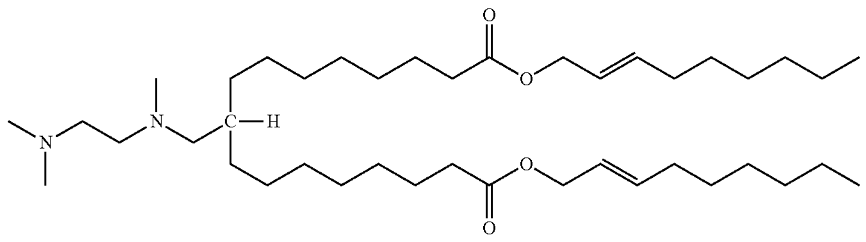

-continued (1-02)

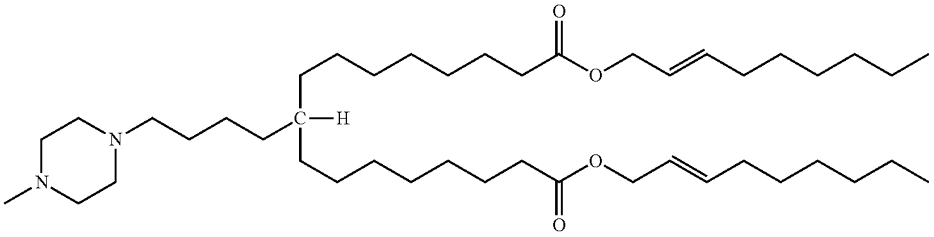

(2-01)

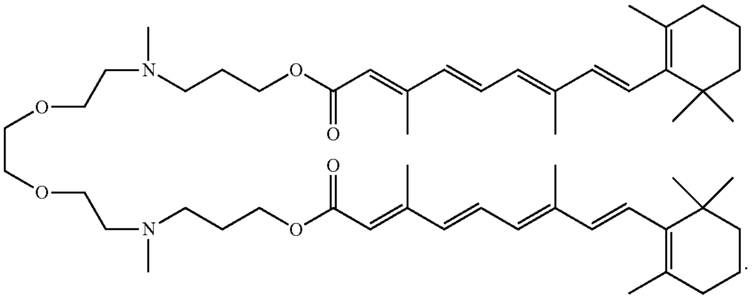

9. The kit according to claim 6, further comprising:
a reagent for detecting expression of the reporter gene.

10. A method for detecting cells having a DNA homologous recombination deficiency, the method comprising: transfecting, into test cells, a first nucleic acid construct including a first promoter sequence and a cleaved Cre gene ligated to downstream of the first promoter sequence and a second nucleic acid construct including a second promoter sequence, a first loxP sequence ligated to downstream of the second promoter sequence, a reporter gene ligated to downstream of the first loxP sequence, and a second loxP sequence ligated to downstream of the reporter gene, wherein the cleaved Cre gene is composed of two Cre gene fragments obtained by cleaving the Cre gene into two parts without deletion of the base sequence of the Cre gene so as to be inactivated, and of the two Cre gene fragments, an upstream gene fragment of the Cre gene is linked downstream of the first promoter sequence, and a downstream gene fragment of the Cre gene is linked upstream of the first promoter sequence; culturing the test cells; and detecting an activity of a protein expressed from the reporter gene, wherein the 5' end of the upstream gene fragment of the Cre gene is linked to a second sequence having a base sequence identical to a portion of the 3' end of the downstream gene fragment of the Cre gene, which is the first sequence, and wherein homologous recombination of the first and second sequences results in a functional Cre gene.

11. The method according to claim 10, wherein the transfecting is performed by bringing the test cells into contact with lipid particles in which the first nucleic acid construct and the second nucleic acid construct are encapsulated.

12. The method according to claim 10, wherein, among the test cells, the activity of the reporter protein is high in cells having a DNA homologous recombination deficiency.

13. The method according to claim 10, wherein the culturing and the detecting are performed on a CMOS image sensor.

14. A method for predicting an effect of a drug, the method comprising: transfecting, into test cells derived from a subject, a first nucleic acid construct comprising a first promoter sequence and a cleaved Cre gene ligated to downstream of the first promoter sequence and a second nucleic acid construct comprising a second promoter sequence, a first loxP sequence ligated to downstream of the second promoter sequence, a reporter gene ligated to downstream of the first loxP sequence, and a second loxP sequence ligated to downstream of the reporter gene, wherein the cleaved Cre gene is composed of two Cre gene fragments obtained by cleaving the Cre gene into two parts without deletion of the base sequence of the Cre gene so as to be inactivated, and of the two Cre gene fragments, an upstream gene fragment of the Cre gene is linked downstream of the first promoter sequence, and a downstream gene fragment of the Cre gene is linked upstream of the first promoter sequence; culturing the test cells; detecting a signal from a protein expressed from the reporter gene; calculating a positive rate of cells having a DNA homologous recombination deficiency included in the test cells based on a result of the detecting; and predicting an effect of a drug which is effective against a cancer with the DNA homologous recombination deficiency on a cancer in the subject based on the positive rate, wherein the 5' end of the upstream gene fragment of the Cre gene is linked to a second sequence having a base sequence identical to a portion of the 3' end of the downstream gene fragment of the Cre gene, which is the first sequence, and wherein homologous recombination of the first and second sequences results in a functional Cre gene.

15. The method according to claim 14, wherein the transfecting is performed by bringing the test cells into contact with lipid particles in which the first nucleic acid construct and the second nucleic acid construct are encapsulated.

16. The method according to claim 14, wherein the culturing and the detecting are performed on a CMOS image sensor.

17. The method according to claim 14, wherein, from the result of the detecting, cells in which the activity of the reporter protein is high among the test cells are to be the cells having the DNA homologous recombination deficiency, and the positive rate of the cells having the DNA homologous recombination deficiency is calculated by the following Equation (I):

Positive rate=number of cells having DNA homologous recombination deficiency/number of test cells, Equation (1).

18. The method according to claim 14, wherein, in the predicting, it is determined that the higher the positive rate is, the greater the effect of the drug is.

* * * * *